US011145396B1

(12) United States Patent
McNair

(10) Patent No.: US 11,145,396 B1
(45) Date of Patent: Oct. 12, 2021

(54) DISCOVERING CONTEXT-SPECIFIC COMPLEXITY AND UTILIZATION SEQUENCES

(71) Applicant: CERNER INNOVATION, INC., Kansas City, KS (US)

(72) Inventor: Douglas S. McNair, Leawood, KS (US)

(73) Assignee: CERNER INNOVATION, INC., Kansas City, KS (US)

(*) Notice: Subject to any disclaimer, the term of this patent is extended or adjusted under 35 U.S.C. 154(b) by 100 days.

(21) Appl. No.: 15/855,720

(22) Filed: Dec. 27, 2017

Related U.S. Application Data

(60) Division of application No. 14/281,593, filed on May 19, 2014, now Pat. No. 10,769,241, which is a
(Continued)

(51) Int. Cl.
*G16H 20/10* (2018.01)
*G16H 10/60* (2018.01)
*G16H 50/20* (2018.01)

(52) U.S. Cl.
CPC ............. *G16H 20/10* (2018.01); *G16H 10/60* (2018.01); *G16H 50/20* (2018.01)

(58) Field of Classification Search
None
See application file for complete search history.

(56) References Cited

U.S. PATENT DOCUMENTS

| 4,839,853 A | 6/1989 | Deerwester et al. |
| 5,243,565 A | 9/1993 | Yamamoto |

(Continued)

FOREIGN PATENT DOCUMENTS

| EP | 1043666 A2 | 10/2000 |
| EP | 2365456 A2 | 9/2011 |

(Continued)

OTHER PUBLICATIONS

Non-Final Office Action dated Dec. 29, 2017 in U.S. Appl. No. 14/555,058, 13 pages.
(Continued)

*Primary Examiner* — Lena Najarian
(74) *Attorney, Agent, or Firm* — Shook, Hardy & Bacon LLP

(57) ABSTRACT

Systems, methods, and computer-readable media are provided for patient case and care complexity characterization, and detecting matches of an individual patient's record with collections of other patients' records, based on serial, longitudinal patterns, for facilitating efficient health services utilization, implementing programs to reduce complexity, preventive medicine, and risk management in health care. In an embodiment, time series are formed by electronically representing information pertaining to successive longitudinal episodes of health services utilization and the circumstances in which the episodes were incurred; calculating time-series K-nearest-neighbor clusters and distances for each combination; determining the cluster to which a given candidate patient complexity record is nearest, and prescribing one or more interventions specific to the plurality of hazards that are characteristic of trajectories that are members of that cluster, or that are deemed to be relevant to mitigating those hazards, thereby preventing the adverse outcomes and subsequent excess utilization that are prevalent in that cluster.

20 Claims, 13 Drawing Sheets

Related U.S. Application Data continuation-in-part of application No. 14/209,568, filed on Mar. 13, 2014, which is a continuation-in-part of application No. 14/175,750, filed on Feb. 7, 2014, now Pat. No. 10,946,311.

(60) Provisional application No. 61/824,377, filed on May 17, 2013, provisional application No. 61/762,178, filed on Feb. 7, 2013.

(56) References Cited

U.S. PATENT DOCUMENTS

| | | | |
|---|---|---|---|
| 5,301,109 A | 4/1994 | Landauer et al. | |
| 5,664,109 A | 9/1997 | Johnson et al. | |
| 5,809,494 A | 9/1998 | Nguyen | |
| 5,835,900 A | 11/1998 | Fagg, III et al. | |
| 6,039,688 A | 3/2000 | Douglas et al. | |
| 6,122,628 A | 9/2000 | Castelli et al. | |
| 6,246,964 B1 | 6/2001 | Blaunstein | |
| 6,246,975 B1 | 6/2001 | Rivonelli et al. | |
| 6,247,004 B1 | 6/2001 | Moukheibir | |
| 6,397,224 B1 | 5/2002 | Zubeldia et al. | |
| 6,618,715 B1 | 9/2003 | Johnson et al. | |
| 6,654,740 B2 | 11/2003 | Tokuda et al. | |
| 6,665,669 B2 | 12/2003 | Han et al. | |
| 6,915,254 B1 | 7/2005 | Heinze et al. | |
| 6,996,575 B2 | 2/2006 | Cox et al. | |
| 7,039,634 B2 | 5/2006 | Xu et al. | |
| 7,120,626 B2 | 10/2006 | Li et al. | |
| 7,249,117 B2 | 7/2007 | Estes | |
| 7,386,522 B1 | 6/2008 | Bigus et al. | |
| 7,440,947 B2 | 10/2008 | Adcock et al. | |
| 7,447,643 B1 | 11/2008 | Olson et al. | |
| 7,496,561 B2 | 2/2009 | Caudill et al. | |
| 7,529,765 B2 | 5/2009 | Brants et al. | |
| 7,555,425 B2 | 6/2009 | Oon | |
| 7,558,778 B2 | 7/2009 | Carus et al. | |
| 7,617,078 B2 | 11/2009 | Rao et al. | |
| 7,640,171 B2 | 12/2009 | Gendron et al. | |
| 7,657,540 B1 | 2/2010 | Bayliss | |
| 7,668,820 B2 | 2/2010 | Zuleba | |
| 7,720,846 B1 | 5/2010 | Bayliss | |
| 7,831,423 B2 | 11/2010 | Schubert | |
| 7,844,449 B2 | 11/2010 | Lin et al. | |
| 7,844,566 B2 | 11/2010 | Wnek | |
| 7,853,456 B2 | 12/2010 | Soto et al. | |
| 7,865,373 B2 | 1/2011 | Punzak et al. | |
| 7,899,764 B2 | 3/2011 | Martin et al. | |
| 7,899,796 B1 | 3/2011 | Borthwick et al. | |
| 7,900,052 B2 | 3/2011 | Jonas | |
| 7,912,842 B1 | 3/2011 | Bayliss | |
| 7,933,909 B2 | 4/2011 | Trepetin | |
| 7,953,685 B2 | 5/2011 | Liu et al. | |
| 8,015,136 B1 | 9/2011 | Baker et al. | |
| 8,078,554 B2 | 12/2011 | Fung et al. | |
| 8,126,736 B2 | 2/2012 | Anderson et al. | |
| 8,160,895 B2 | 4/2012 | Schmitt et al. | |
| 8,165,893 B1 | 4/2012 | Goldberg et al. | |
| 8,200,505 B2 | 6/2012 | Walker et al. | |
| 8,515,777 B1 | 8/2013 | Rajasenan | |
| 8,539,424 B2 | 9/2013 | Tetelbaum | |
| 8,589,424 B1 | 11/2013 | Patel et al. | |
| 8,666,785 B2 | 3/2014 | Baluta et al. | |
| 8,838,628 B2 | 9/2014 | Leighton et al. | |
| 8,856,156 B1 | 10/2014 | McNair et al. | |
| 9,375,142 B2 | 6/2016 | Schultz et al. | |
| 9,542,532 B1 | 1/2017 | McNair et al. | |
| 9,542,647 B1 | 1/2017 | Mirhaji | |
| 9,734,146 B1 | 8/2017 | McNair et al. | |
| 10,198,499 B1 | 2/2019 | McNair et al. | |
| 10,249,385 B1 | 4/2019 | McNair et al. | |
| 10,268,687 B1 | 4/2019 | McNair et al. | |
| 10,431,336 B1 | 10/2019 | Murrish et al. | |
| 10,446,273 B1 | 10/2019 | Mcnair et al. | |
| 10,483,003 B1 | 11/2019 | McNair et al. | |
| 10,580,524 B1 | 3/2020 | McNair et al. | |
| 10,628,553 B1 | 4/2020 | Murrish et al. | |
| 10,854,334 B1 | 12/2020 | McNair et al. | |
| 10,957,449 B1 | 3/2021 | McNair et al. | |
| 2002/0032583 A1 | 3/2002 | Joao | |
| 2002/0035486 A1 | 3/2002 | Huyn et al. | |
| 2002/0038227 A1 | 3/2002 | Fey et al. | |
| 2002/0038308 A1 | 3/2002 | Cappi | |
| 2002/0042793 A1 | 4/2002 | Choi | |
| 2002/0073138 A1 | 6/2002 | Gilbert et al. | |
| 2002/0128860 A1 | 9/2002 | Leveque et al. | |
| 2003/0023571 A1 | 1/2003 | Barnhill | |
| 2003/0038308 A1 | 2/2003 | Kim | |
| 2003/0163057 A1 | 8/2003 | Flick et al. | |
| 2003/0212580 A1 | 11/2003 | Shen | |
| 2004/0199332 A1 | 10/2004 | Iliff | |
| 2004/0230105 A1* | 11/2004 | Geva | A61B 5/04012 600/301 |
| 2004/0260666 A1* | 12/2004 | Pestotnik | G16H 50/20 706/46 |
| 2005/0027562 A1 | 2/2005 | Brown | |
| 2005/0049497 A1 | 3/2005 | Krishnan et al. | |
| 2005/0119534 A1 | 6/2005 | Trost et al. | |
| 2005/0144042 A1 | 6/2005 | Joffe et al. | |
| 2005/0288910 A1* | 12/2005 | Schlessinger | G16H 50/50 703/2 |
| 2006/0020465 A1 | 1/2006 | Cousineau et al. | |
| 2006/0064447 A1 | 3/2006 | Malkov | |
| 2006/0074824 A1 | 4/2006 | Li | |
| 2006/0129427 A1 | 6/2006 | Wennberg | |
| 2006/0161457 A1 | 7/2006 | Rapaport et al. | |
| 2006/0173663 A1 | 8/2006 | Langheier et al. | |
| 2006/0205564 A1 | 9/2006 | Peterson | |
| 2006/0206027 A1 | 9/2006 | Malone | |
| 2006/0206359 A1 | 9/2006 | Stang | |
| 2006/0218010 A1 | 9/2006 | Michon et al. | |
| 2006/0271556 A1 | 11/2006 | Mukherjee et al. | |
| 2007/0005621 A1 | 1/2007 | Lesh et al. | |
| 2007/0026365 A1 | 2/2007 | Friedrich et al. | |
| 2007/0031873 A1 | 2/2007 | Wang et al. | |
| 2007/0094048 A1 | 4/2007 | Grichnik | |
| 2007/0106533 A1 | 5/2007 | Greene | |
| 2007/0106752 A1 | 5/2007 | Moore | |
| 2007/0233391 A1 | 10/2007 | Milstein et al. | |
| 2007/0239482 A1 | 10/2007 | Finn et al. | |
| 2007/0244724 A1 | 10/2007 | Pendergast et al. | |
| 2008/0021288 A1 | 1/2008 | Bowman et al. | |
| 2008/0046292 A1 | 2/2008 | Myers et al. | |
| 2008/0097938 A1 | 4/2008 | Guyon et al. | |
| 2008/0131374 A1 | 6/2008 | Medich et al. | |
| 2008/0133269 A1 | 6/2008 | Ching | |
| 2008/0147441 A1 | 6/2008 | Kil | |
| 2008/0172214 A1 | 7/2008 | Col et al. | |
| 2008/0172251 A1 | 7/2008 | Reichert et al. | |
| 2008/0183454 A1 | 7/2008 | Barabasi et al. | |
| 2008/0195422 A1 | 8/2008 | Nessinger et al. | |
| 2008/0243548 A1 | 10/2008 | Cafer | |
| 2008/0249376 A1 | 10/2008 | Zaleski | |
| 2008/0255884 A1 | 10/2008 | Carus et al. | |
| 2008/0256006 A1 | 10/2008 | Buscema et al. | |
| 2008/0268413 A1 | 10/2008 | Leichner | |
| 2008/0275731 A1 | 11/2008 | Rao et al. | |
| 2008/0287746 A1 | 11/2008 | Reisman | |
| 2008/0288292 A1 | 11/2008 | Bi et al. | |
| 2008/0288474 A1 | 11/2008 | Chin et al. | |
| 2008/0294692 A1* | 11/2008 | Angell | G16H 50/70 |
| 2008/0301177 A1 | 12/2008 | Doherty | |
| 2008/0306926 A1 | 12/2008 | Friedlander et al. | |
| 2009/0006431 A1 | 1/2009 | Agrawal et al. | |
| 2009/0012928 A1 | 1/2009 | Lussier et al. | |
| 2009/0112892 A1 | 4/2009 | Cardie et al. | |
| 2009/0125333 A1 | 5/2009 | Heywood et al. | |
| 2009/0132284 A1 | 5/2009 | Fey et al. | |
| 2009/0164249 A1 | 6/2009 | Hunt et al. | |
| 2009/0228303 A1 | 9/2009 | Faulkner et al. | |
| 2009/0259493 A1 | 10/2009 | Venon et al. | |
| 2009/0299767 A1 | 12/2009 | Michon et al. | |
| 2009/0299977 A1 | 12/2009 | Rosales | |
| 2009/0304246 A1 | 12/2009 | Walker et al. | |

(56) References Cited

U.S. PATENT DOCUMENTS

| | | |
|---|---|---|
| 2009/0313041 A1 | 12/2009 | Eder |
| 2009/0318775 A1 | 12/2009 | Michelson et al. |
| 2009/0319295 A1 | 12/2009 | Kass-Hout et al. |
| 2010/0082369 A1 | 4/2010 | Prenelus et al. |
| 2010/0088117 A1 | 4/2010 | Belden et al. |
| 2010/0131434 A1 | 5/2010 | Magent et al. |
| 2010/0131438 A1 | 5/2010 | Pandya et al. |
| 2010/0131482 A1 | 5/2010 | Linthicum et al. |
| 2010/0131883 A1 | 5/2010 | Linthicum et al. |
| 2010/0142774 A1 | 6/2010 | Ben-Haim et al. |
| 2010/0145720 A1 | 6/2010 | Reiner |
| 2010/0179818 A1 | 7/2010 | Kelly et al. |
| 2010/0185685 A1 | 7/2010 | Chew et al. |
| 2010/0198755 A1 | 8/2010 | Soll et al. |
| 2010/0274576 A1 | 10/2010 | Young |
| 2010/0293003 A1 | 11/2010 | Abbo |
| 2010/0299155 A1 | 11/2010 | Findlay et al. |
| 2010/0324861 A1 | 12/2010 | Goulding et al. |
| 2010/0324938 A1 | 12/2010 | Ennett et al. |
| 2011/0010401 A1 | 1/2011 | Adams et al. |
| 2011/0015937 A1 | 1/2011 | Janas et al. |
| 2011/0046979 A1 | 2/2011 | Tulipano et al. |
| 2011/0067108 A1 | 3/2011 | Hoglund |
| 2011/0077973 A1 | 3/2011 | Breitenstein et al. |
| 2011/0087501 A1 | 4/2011 | Severin |
| 2011/0093467 A1 | 4/2011 | Sharp et al. |
| 2011/0119089 A1 | 5/2011 | Carlisle |
| 2011/0161110 A1 | 6/2011 | Mault |
| 2011/0201900 A1 | 8/2011 | Zhang et al. |
| 2011/0225001 A1 | 9/2011 | Shen |
| 2011/0246238 A1 | 10/2011 | Vdovjak et al. |
| 2011/0270629 A1 | 11/2011 | Abbo |
| 2011/0295621 A1 | 12/2011 | Farooq et al. |
| 2011/0306845 A1 | 12/2011 | Osorio |
| 2012/0016685 A1* | 1/2012 | Ryan ............... G06F 19/3456 705/2 |
| 2012/0020536 A1 | 1/2012 | Moehrle |
| 2012/0047105 A1 | 2/2012 | Saigal et al. |
| 2012/0059779 A1 | 3/2012 | Syed et al. |
| 2012/0072235 A1 | 3/2012 | Varadarajan et al. |
| 2012/0078127 A1 | 3/2012 | McDonald et al. |
| 2012/0086963 A1 | 4/2012 | Fujitsuka et al. |
| 2012/0089420 A1 | 4/2012 | Hoffman et al. |
| 2012/0089421 A1 | 4/2012 | Hoffman et al. |
| 2012/0095780 A1 | 4/2012 | McNair |
| 2012/0110016 A1 | 5/2012 | Phillips |
| 2012/0173475 A1 | 7/2012 | Ash et al. |
| 2012/0174014 A1 | 7/2012 | Ash et al. |
| 2012/0174018 A1 | 7/2012 | Ash et al. |
| 2012/0175475 A1 | 7/2012 | McErlane |
| 2012/0203575 A1 | 8/2012 | Tulipano et al. |
| 2012/0215784 A1 | 8/2012 | King et al. |
| 2012/0232930 A1 | 9/2012 | Schmidt et al. |
| 2012/0246102 A1 | 9/2012 | Sudharsan |
| 2013/0006911 A1 | 1/2013 | Christie, IV et al. |
| 2013/0023434 A1 | 1/2013 | Van Laar |
| 2013/0046529 A1 | 2/2013 | Grain et al. |
| 2013/0046558 A1 | 2/2013 | Landi et al. |
| 2013/0110547 A1 | 5/2013 | Englund et al. |
| 2013/0110548 A1 | 5/2013 | Kutty |
| 2013/0132312 A1 | 5/2013 | Lee et al. |
| 2013/0132323 A1 | 5/2013 | Soto et al. |
| 2013/0197938 A1 | 8/2013 | Bayouk et al. |
| 2013/0245389 A1 | 9/2013 | Schultz et al. |
| 2014/0081652 A1 | 3/2014 | Klindworth |
| 2014/0095184 A1 | 4/2014 | Gotz et al. |
| 2014/0095186 A1 | 4/2014 | Gotz et al. |
| 2014/0180699 A1 | 6/2014 | Massa et al. |
| 2014/0181128 A1 | 6/2014 | Riskin et al. |
| 2014/0200414 A1 | 7/2014 | Osorio |
| 2014/0336539 A1 | 11/2014 | Torres et al. |
| 2015/0049947 A1 | 2/2015 | Katsaros et al. |
| 2015/0161329 A1 | 6/2015 | Mabotuwana et al. |
| 2015/0193583 A1 | 7/2015 | McNair et al. |
| 2015/0254408 A1 | 9/2015 | Mahtani et al. |
| 2015/0324535 A1 | 11/2015 | Ash et al. |
| 2015/0363559 A1 | 12/2015 | Jackson et al. |
| 2016/0004840 A1 | 1/2016 | Rust et al. |
| 2016/0063212 A1 | 3/2016 | Monier et al. |
| 2016/0143594 A1 | 5/2016 | Moorman et al. |
| 2017/0124269 A1 | 5/2017 | McNair et al. |
| 2020/0043612 A1 | 2/2020 | McNair et al. |
| 2020/0335179 A1 | 10/2020 | Stojadinovic et al. |

FOREIGN PATENT DOCUMENTS

| | | | |
|---|---|---|---|
| WO | WO-2006002465 A1 * | 1/2006 | ............. G16H 50/70 |
| WO | 2012/122122 A1 | 9/2012 | |
| WO | 2012122195 A1 | 9/2012 | |
| WO | 2012122196 A2 | 9/2012 | |

OTHER PUBLICATIONS

Final Office Action dated May 1, 2018 in U.S. Appl. No. 14/148,046, 31 pages.

Non-Final Office Action dated May 3, 2018 in U.S. Appl. No. 15/392,928, 15 pages.

Non-Final Office Action dated Jun. 28, 2018 in U.S. Appl. No. 14/148,059, 27 pages.

Final Office Action dated Jun. 29, 2018 in U.S. Appl. No. 13/963,732, 22 pages.

Final Office Action dated Sep. 7, 2018 in U.S. Appl. No. 14/555,058, 19 pages.

Non-Final Office Action received for U.S. Appl. No. 14/148,059, dated Apr. 26, 2019, 28 pages.

Non-Final Office Action received for U.S. Appl. No. 14/792,736, dated Apr. 11, 2019, 18 pages.

Non-Final Office Action received for U.S. Appl. No. 14/982,982, dated May 14, 2019, 9 pages.

Arpaia et al, "Multi-Agent Remote Predictive Diagnosis of Dangerous Good Transports", Instrumentation and Measurement Technology Conference, Proceedings of the IEEE, May 17-19, 2005, pp. 1685-1690.

Non-Final Office Action received for U.S. Appl. No. 14/555,058, dated Jun. 25, 2019, 20 pages.

Non-Final Office Action received for U.S. Appl. No. 13/963,732, dated Jul. 11, 2019, 13 pages.

Non-Final Office Action received for U.S. Appl. No. 14/148,046, dated Jun. 24, 2019, 27 pages.

Agrawal R, et al. 'Fast Discovery of Association Rules.' In Fayyad U, et al., eds., Advances in Knowledge Discovery and Data Mining, pp. 307328. Menlo Park, AAAI Press, 1996.

Dvorak J, et al. Risk Factor Analysis for Injuries in Football Players: Possibilities for a Prevention Program. Am J Sports Med. 2000;28:S69-74.

Huyse, Frits et al., Compri—An Instrument to Detect Patients With Complex Care Needs; Psychosomatics 42:3, May-Jun. 2001; 7 pages.

Billari F, et al. Timing, Sequencing, and quantum of Life Course Events: A Machine-Learning Approach. Eur J Pop 2006;22:3765.

Han J-W, et al. Frequent Pattern Mining: Current status and future directions. Data Mining and Knowledge Discovery 2007;15:55-86.

Kiran, R. Uday, and P. Krishna RE. "An improved multiple minimum support based approach to mine rare association rules." Computational Intelligence and Data Mining, 2009. CIDM'09. IEEE Symposium on. IEEE, 2009.

Murat Sariyar and Andreas Borg, The Recordlinkage Package: Detecting Errors in Data, Dec. 2010, The R Journal vol. 212, pp. 61-67.

Ohno-Machado, Lucila; "Realizing the full potential of electronic health records: the role of natural language processing", Sep. 2011, Journal of American Medical Information Association, vol. 18 No. 5, p. 539.

Cohen, Eyal et al., Integrated Complex Care Coordination for Children With Medical Complexity: A Mixed-Methods Evaluation of Tertiary Care-Community Collaboration; BioMed Central The Open Access Publisher; www.biomedcentral.com/1472-6963/12/366; Oct. 23, 2012; 23 pages.

(56) References Cited

OTHER PUBLICATIONS

Berry, Leonard et al., Care Coordination for Patients With Complex Health Profiles in Inpatients and Outpatient Settings; Mayo Clinic Proceedings; www.mayoclinicproceedings.org; Jan. 11, 2013; 11 pages.
Non-Final Office Action dated Dec. 27, 2017 in U.S. Appl. No. 13/963,732, 18 pages.
Final Office Action dated Feb. 16, 2018 in U.S. Appl. No. 14/281,593, 15 pages.
Final Office Action dated Jan. 26, 2018 in U.S. Appl. No. 14/148,039, 33 pages.
Final Office Action dated Jan. 5, 2018 in U.S. Appl. No. 14/148,028, 32 pages.
Final Office dated Jan. 18, 2018 in U.S. Appl. No. 14/147,978, 28 pages.
Non-Final Office Action dated Mar. 2, 2018 in U.S. Appl. No. 14/209,568, 23 pages.
Abbott A, Tsay A. Sequence Analysis and Optimal Matching Methods in Sociology, Review and Prospect. Sociol Meth Res 2000;29:3-33.
Berchtold A, Raftery A. The Mixture Transition Distribution Model for High-Order Markov Chains and Non-Gaussian Time Series. Stat Sci 2002;17:328-56.
Deville J, Saporta G. Correspondence Analysis with an Extension Towards Nominal Time Series. J Econometrics 1983;22:169-89.
Dijkstra W, Tanis T. Measuring the Agreement Between Sequences. Sociol Meth Res 1995;24:214-31.
Dvorak, Junge A. Football Injuries and Physical Symptoms: A Review of the Literature. Am J Sports Med 2000;28:S3-9.
Dvorak, Junge A.. Soccer Injuries: A Review on Incidence and Prevention. Sports Med. 2004;34:929-38.
Hawkins R, Fuller C. A Prospective Epidemiological Study of Injuries in Four English Professional Football Clubs. Br J Sports Med 1999;33:196-203.
Nielsen A, Yde J. Epidemiology and Traumatology of Injuries in Soccer. Am J Sports Med 1989;17:803-7.
Zaki M. Spade: An Efficient Algorithm for Mining Frequent Sequences. Machine Learning 2001;42:31-60.
Nealon, et al.: Agent-Based Applications in Health Care, Department of Computing, Oxford Brookes University and Computer Science and Mathematics Department, University Rovira I Virgill, 17 pages.
Kang, et al.: Mining Based Decision Support Multi-agent System for Personalized e-Healthcare Service*, Schook of Computer Engineering, Sungkyunkwan University, 10 pages.
Mabry, et al.: Clinical Decision Support with IM-Agents and ERMA Multi-agents, Department of Computer Science and Emergency Medicine, 6 pages.
Christian Roever, Package 'bspec', Feb. 21, 2013, r-project.org, pp. 1-27.
Final Office Action dated Jan. 4, 2018 in U.S. Appl. No. 14/147,991, 35 pages.
Final Office Action dated Apr. 2, 2018 in U.S. Appl. No. 14/148,050, 24 pages.
Final Office Action dated Apr. 2, 2018 in U.S. Appl. No. 14/148,020, 21 pages.
Non-Final Office Action dated Apr. 13, 2018 in U.S. Appl. No. 13/647,187, 27 pages.
First Action Interview Office Action dated Apr. 17, 2018 in U.S. Appl. No. 14/792,736, 24 pages.
Aronson, Alan R., "MetaMap: Mapping Text to the UMLS Metathesaurus", 2006, pp. 1-26.
Final Office action received for U.S. Appl. No. 13/647,187, dated Dec. 14, 2018, 28 pages.
Non-Final Office Action received for U.S. Appl. No. 14/147,991, dated Nov. 27, 2018, 37 pages.
Final Office Action received for U.S. Appl. No. 13/647,187, dated May 3, 2016, 19 pages.
Final Office Action received for U.S. Appl. No. 14/148,020, dated Jul. 29, 2016, 23 pages.
Final Office Action received for U.S. Appl. No. 14/148,050, dated Sep. 9, 2016, 23 pages.
Final Office Action received for U.S. Appl. No. 14/209,568, dated Jun. 16, 2017, 20 pages.
Final Office Action received for U.S. Appl. No. 14/792,736, dated Oct. 15, 2018, 18 pages.
Non-Final Office Action received for U.S. Appl. No. 12/982,131, dated Dec. 20, 2013, 19 pages.
Non-Final Office Action received for U.S. Appl. No. 14/147,978, dated Sep. 28, 2018, 29 pages.
Non-Final Office Action received for U.S. Appl. No. 14/147,978, dated May 18, 2017, 29 pages.
Non-Final Office Action received for U.S. Appl. No. 14/477,284, dated Aug. 5, 2015, 11 pages.
Notice of Allowance received for U.S. Appl. No. 13/874,961, dated Oct. 15, 2018, 9 pages.
Preinterview First Office Action Received for U.S. Appl. No. 14/792,736, dated Dec. 8, 2017, 22 pages.
Final Office Action in Related U.S. Appl. No. 14/148,002, dated May 30, 2018, 29 Pages.
Final Office Action in Related U.S. Appl. No. 13/250,072, dated May 31, 2018, 20 Pages.
Final Office Action in Related U.S. Appl. No. 14/175,750, dated Jun. 13, 2018, 11 Pages.
Final Office Action received for U.S. Appl. No. 14/148,020, dated Oct. 9, 2019, 25 pages.
Final Office Action received for U.S. Appl. No. 14/555,058, dated Feb. 12, 2020, 22 pages.
First Action Interview Office Action received for U.S. Appl. No. 15/386,876, dated Jan. 28, 2020, 24 pages.
Non-Final Office Action received for U.S. Appl. No. 13/269,244, dated Apr. 8, 2020, 17 pages.
Appavoo et al., "Enabling Autonomic Behavior in Systems Software With Hot Swapping", IBM Systems Journal, vol. 42, No. 1, 2003, pp. 60-76.
Final Office Action received for U.S. Appl. No. 13/269,244, dated Aug. 12, 2020, 18 pages.
Final Office Action received for U.S. Appl. No. 14/148,059, dated Jul. 16, 2020, 16 pages.
Notice of Allowance received for U.S. Appl. No. 14/148,020, dated Jul. 22, 2020, 10 pages.
Townsend, Hilary, "Natural Language Processing and Clinical Outcomes: The Promise and Progress of NLP for Improved Care", Journal of AHIMA, vol. 84, No. 2, Available online at: <https://bok.ahima.org/doc?oid=106198#.X0SgnSgzY2x>, Mar. 2013, 3 pages.
Non-Final Office Action received for U.S. Appl. No. 16/819,890, dated Sep. 29, 2020, 12 pages.
Non-Final Office Action received for U.S. Appl. No. 15/386,876, dated Sep. 14, 2020, 15 pages.
Notice of Allowance received for U.S. Appl. No. 14/148,046, dated Oct. 7, 2020, 11 pages.
The Comprehensive R Archive Network, R, Available online at: <http://cran.r-project.org>, Retrieved on Feb. 27, 2020, 1 page.
Cook et al., "Making Prophecies with Decision Predicates", ACM 978-1-4503-0490-0/11/01, Jan. 2011, 14 pages.
Prados-Suarez et al., "Contextualized Access to Electronical Health Records in Cardiology", IEEE Transactions on Information Technology in Biomedicine, vol. 16, No. 3, doi: 10.1109/TITB.2011.2178033., May 2012, pp. 401-412.
Final Office Action received for U.S. Appl. No. 14/148,039, dated Feb. 1, 2021, 17 pages.
Final Office Action received for U.S. Appl. No. 15/386,876, dated Jan. 11, 2021, 16 pages.
Non-Final Office Action received for U.S. Appl. No. 16/868,642, dated Feb. 4, 2021, 24 pages.
Summons to Attend Oral Proceedings received for European Patent Application No. 14835964.9, mailed on Jan. 13, 2021, 12 pages.
Abernethy et al., "Eliciting Consumer Preferences Using Robust Adaptive Choice Questionnaires", IEEE Transactions on Knowledge and Data Engineering, vol. 20, No. 2, Feb. 2008, pp. 145-155.
Othman et al., "Agent Based Preprocessing", International Conference on Intelligent and Advanced Systems 2007, 2007, pp. 219-223.

(56) References Cited

OTHER PUBLICATIONS

Ta et al., "Data Descriptor: Columbia Open Health Data, Clinical Concept Prevalence and Co-occurrence from Electronic Health Records", Scientific data, vol. 5, 180273, doi: 10.1038/sdata.2018.273, Nov. 27, 2018, pp. 1-17.

Uhrmacher et al., "Distributed, Parallel Simulation of Multiple, Deliberative Agents", Proceedings of the fourteenth workshop on Parallel and distributed simulation, May 2000, pp. 101-108.

Notice of Allowance received for U.S. Appl. No. 16/588,647, dated Apr. 1, 2021, 21 pages.

Final Office action received for U.S. Appl. No. 14/555,058, dated Jun. 22, 2021, 12 pages.

Non-Final Office Action received for U.S. Appl. No. 16/819,890, dated Jun. 24, 2021, 14 pages.

Preinterview First Office Action received for U.S. Appl. No. 16/601,311, dated Jun. 15, 2021, 4 pages.

Shirabad et al., "Implementing an Integrative Multi-agent Clinical Decision Support System with Open Source Software", J Med Syst 36, Available online at: <https://doi.org/10.1007/s10916-010-9452-9>, 2012, pp. 123-137.

Final Office Action received for U.S. Appl. No. 14/209,568, dated Jul. 12, 2021, 9 pages.

Non-Final Office action received for U.S. Appl. No. 16/237,304, dated Jul. 7, 2021, 13 pages.

Duff, Iain S., "Development and history of sparse direct methods", SIAM Conference on Applied Linear Algebra, Available online at: <http://www,numerical.rl.ac.uk/people/isd/isd,html>, Oct. 26-29, 2009, 44 pages.

Xue et al., "Fast Query by Example of Environmental Sounds via Robust and Efficient Cluster-based Indexing", 2008 EEE, International Conference on Acoustics, Speech and Signal Processing, Available online at: <doi: 10.1109/ICASSP.2008.4517532>, 2008, pp. 5-8.

* cited by examiner

| Patient in in-patient venue or in ED venue… | enter |
|---|---|
| Doctor: | |
| • Do you expect this hospital stay will last 2 weeks or more? (Y/N) | N |
| • Do you think the organization of care during this hospital stay will be complex? (Y/N) | Y |
| • Do you expect that this patient's mental health will be disturbed during this hospital stay? (Y/N) | Y |
| Nurse: | |
| • Do you expect this hospital stay will last 2 weeks or more? (Y/N) | N |
| • Do you think the organization of care during this hospital stay will be complex? (Y/N) | Y |
| • Do you think this patient will be limited in activities of daily living after discharge? (Y/N) | Y |
| Additional info (from EMR or other sources): | |
| • Is this an unplanned acute-care episode? (N/Y) | Y |
| • Is the patient retired or unemployed? (Y/N) | Y |
| • Is the patient known to currently active malignancy? (Y/N) | N |
| • Did the patient have walking difficulties during the last 3 months? (Y/N) | N |
| • Did the patient have a negative health perception during the last week? (Y/N) | Y |
| • Number of doctor visits during the past three months? | 7 |
| • Number of different kinds of medications in the prescribed meds regimen as of the day prior to this episode? | 4 |
| evaluate | results |
| data complete? | Yes |
| COMPRI | 9 |

| | etc |
|---|---|
| • Frequency per day | |
| • Dosage different for doses within same day? (Y/N) | N |
| • At different time from other meds? (Y/N) | Y |
| • Take before getting up from sleep? (Y/N) | N |
| • Dosage changes based on self-testing? (Y/N) | N |
| • Doses different on alternate days? (Y/N) | N |
| • Other special instructions? (Y/N) | N |
| • Number of times each day this activity is required with this med: | |
| • Take with food | 3 |
| • Break tablets into smaller pieces | 0 |
| • Crush tablets or open and empty capsules | 0 |
| • Mix into food (pudding, applesauce, etc.) or beverage | 0 |
| • Take on empty stomach | 3 |
| • Take 2 or more different strength tablets when taking one dose | 0 |
| • Take more than 1 tablet when taking one dose | 3 |
| • Apply cream/ointment/drops formulation | 0 |
| • Inject subcutaneously/intramuscularly | 0 |
| • Inhale aerosol/dry powder inhaler | 0 |
| • Administer per rectum | 0 |
| • Administer according to other special instructions | 0 |
| evaluate | results |
| data complete? | Yes |
| kind for this med | ? |

| ID | NbrChrtDx | AgeGrp | Medicaid/SSI | CumLawEn | w.01 | w.02 | w.03 | w.04 | w.05 | w.06 | w.07 | w.08 | w.09 | w.10 | w.11 | w.12 | w.13 | w.14 | w.15 |
|---|---|---|---|---|---|---|---|---|---|---|---|---|---|---|---|---|---|---|---|
| | 3 | 40-59 | N | 0 | 00x | 00x | 00x | 00x | 00x | 00x | 00x | 08x | 08x | 08x | 08x | 08x | 08x | 08x | 08x |
| | 5 | 40-59 | Y | 1 | 03x | 03x | 03x | 03x | 03x | 03x | 03x | 1Fx | 0Ax | 0Ax | 0Ax | 0Ax | 0Ax | 0Ax | 0Ax |
| | 1 | 20-39 | N | 2 | 00x | 1Fx | 00x | 00x | 00x | 00x | 00x | 00x | 00x | 00x | 00x | 00x | 00x | 00x | 00x |
| | 4 | 20-39 | Y | 0 | 00x | 00x | 00x | 00x | 00x | 00x | 00x | 00x | 3Fx | 00x | 00x | 00x | 00x | 05x | 05x |
| | 3 | 80+ | N | 0 | 00x | 00x | 00x | 00x | 00x | 00x | 00x | 00x | 00x | 00x | 00x | 00x | 00x | 00x | 00x |
| | 2 | 40-59 | Y | 1 | 00x | 00x | 00x | 00x | 00x | 00x | 00x | 00x | 00x | 00x | 00x | 00x | 00x | 00x | 00x |
| | 1 | 20-39 | N | 0 | 00x | 00x | 00x | 00x | 00x | 00x | 00x | 00x | 00x | 3Fx | 3Fx | 3Fx | 3Fx | 3Fx | 3Fx |
| | 3 | 40-59 | Y | 1 | 00x | 00x | 00x | 00x | 00x | 00x | 00x | 00x | 00x | 00x | 00x | 00x | 1Fx | 05x | 05x |
| | 5 | 60-79 | N | 3 | 00x | 00x | 00x | 00x | 00x | 00x | 00x | 00x | 00x | 00x | 00x | 00x | 00x | 00x | 1Fx |
| | 2 | 20-39 | Y | 0 | 00x | 00x | 00x | 00x | 0Ax | 00x | 00x | 00x | 00x | 00x | 00x | 00x | 00x | 00x | 00x |
| | 9 | 80+ | N | 0 | 00x | 00x | 00x | 00x | 00x | 00x | 00x | 00x | 00x | 00x | 00x | 00x | 00x | 00x | 00x |

| w.16 | w.17 | w.18 | w.19 | w.20 | w.21 | w.22 | w.23 | w.24 | w.25 | w.26 | w.27 | w.28 | w.29 | w.30 | w.31 | w.32 | w.33 | w.34 | w.35 | w.36 | w.37 | w.38 | w.3... |
|---|---|---|---|---|---|---|---|---|---|---|---|---|---|---|---|---|---|---|---|---|---|---|---|
| 08x | 08x | 08x | 08x | 08x | 08x | 08x | 08x | 08x | 00x | 00x | 03x | 03x | 03x | 03x | 03x | 03x | 03x | 03x | 03x | 03x | 03x | 03x | 03x |
| 0Ax | 0Ax | 0Ax | 03x | 03x | 03x | 05x | 05x | 05x | 05x | 05x | 05x | 05x | 05x | 05x | 05x | 05x | 05x | 05x | 05x | 05x | 05x | 05x | 05x |
| 00x | 1Fx | 03x | 05x | 05x | 05x | 03x | 05x | 05x | 03x | 05x | 00x | 1Fx | 03x | 00x | 00x | 00x | 00x | 1Fx | 00x | 00x | 00x | 00x | 00x |
| 05x | 05x | 00x | 00x | 00x | 00x | 03x | 03x | 03x | 03x | 03x | 03x | 05x | 03x | 03x | 03x | 03x | 05x | 05x | 3Fx | 05x | 05x | 05x | 03x |
| 00x | 00x | 00x | 00x | 00x | 00x | 00x | 00x | 1Fx | 00x | 00x | 00x | 3Fx | 3Fx | 00x | 00x | 00x | 00x | 00x | 00x | 00x | 00x | 00x | 00x |
| 00x | 00x | 00x | 00x | 3Fx | 00x | 00x | 00x | 00x | 00x | 00x | 00x | 00x | 00x | 00x | 00x | 00x | 00x | 00x | 00x | 00x | 00x | 00x | 00x |
| 3Fx | 3Fx | 3Fx | 00x | 00x | 03x | 00x | 1Fx | 00x | 00x | 00x | 00x | 00x | 00x | 00x | 00x | 00x | 00x | 00x | 00x | 0Fx | 00x | 00x | 00x |
| 05x | 1Fx | 1Fx | 1Fx | 1Fx | 1Fx | 1Fx | 1Fx | 1Fx | 1Fx | 00x | 00x | 00x | 00x | 00x | 00x | 00x | 00x | 00x | 00x | 00x | 00x | 00x | 00x |
| 1Fx | 00x | 00x | 00x | 00x | 00x | 00x | 00x | 00x | 00x | 00x | 3Fx | 00x | 00x | 00x | 00x | 00x | 00x | 0Ax | 00x | 00x | 00x | 00x | 00x |
| 00x | 00x | 00x | 00x | 00x | 00x | 00x | 00x | 00x | 00x | 00x | 00x | 00x | 00x | 00x | 00x | 00x | 00x | 00x | 00x | 00x | 00x | 00x | 00x |
| 00x | 00x | 00x | 00x | 00x | 00x | 00x | 00x | 00x | 00x | 00x | 00x | 00x | 00x | 00x | 00x | 00x | 00x | 00x | 00x | 00x | 00x | 00x | 00x |

600

```
# DSM 08-DEC-2012
# statistical trajectory mining to discover significant longitudinal patterns in ANMC 2012 dataset
# admissions are lognormally-distributed rlnorm(300, 0.2, 1.5)
# complexity != number of different chronic conditions, severity of illness, principal diagnosis at disch,
payer group, cum law enf enc/10yr
# prefer to have 2-yr hx of episodes, possibly collapse to max in fortnightly or monthly intervals instead
of weekly

library("TraMineR")
library("cluster")
# dsm_anmc_traminer <- read.csv(file.choose())

# transfer data.frame from dsm_care_complexity_TraMineR.xlsx
# NbrDx, AgeGrp, Medicaid_SSI, CumLawEnf, segmented_interventions_complexity_ts (pooling
meds_procedures, encounters by week)

# represent weekly care complexity scores (8-bit hexadecimal; MSN=admission to hosp or unsched ED
visit; LSN=max within-week MCI meds complexity index)
# collapsed to 31-state 2-nybble segmented score where acute-care episode causes LSN to be ORed
with 1's:   000d,001d,002d,003d,004d,005d,006d,007d,

008d,009d,010d,011d,012d,013d,014d,015d,031d,047d,063d,079d,095d,111d,127d,143d,159d,175d,191d,20
7d,223d,239d,255d
#anmc.alphab <-
c("00x","01x","02x","03x","04x","05x","06x","07x","08x","09x","0Ax","0Bx","0Cx","0Dx","0Ex","0Fx",

"1Fx","2Fx","3Fx","4Fx","5Fx","6Fx","7Fx","8Fx","9Fx","AFx","BFx","CFx","DFx","EFx","FFx")
# cpal() required to assign palette if nbr_states > 12
anmc.alphab <- c("00x","03x","05x","08x","0Ax","0Ex","1Fx","3Fx","5Fx","BFx","DFx","FFx")

# generate state-sequences from data frame
anmc.seq <- seqdef(dsm_anmc_traminer, 6:57, xtstep=12, alphabet=anmc.alphab)

# generate state-sequence distance array using seqsubm build method transition-rate "TRATE"
# and substitution-cost matrix optimal-matching "OM" algorithm
anmc.om <- seqdist(anmc.seq, method="OM", indel=1, sm="TRATE")
# anmc.om <- seqdist(anmc.seq, method="OM", indel=1, sm=scost)

# generate statistically most significant top 5 clusters using distance array
# and agglomerative nesting algorithm (agnes) [hierarchical clustering]
# Kaufman L, Rousseeuw P. Finding Groups in Data: An Introduction to Cluster Analysis. Wiley, 1990.
# Struyf A, et al. Integrating Robust Clustering Techniques in S-PLUS. Comput Stat Data Anal
1997;26:17-37.
anmc.clusters <- agnes(anmc.om, diss=TRUE, method="ward")
anmc.clus5 <- cutree(anmc.clusters, k=5)

# retrieve cluster assignment of individual cases (indexed by row in data.frame dsm_anmc_traminer)
# Example: ssi 2012 case id=85, index=35
anmc.clus5[35]

# compute complexity index of individual case sequence/trajectory
anmc.ci35 <- seqici(anmc.seq[35])
```

CONTINUES IN FIG. 7B

FIG. 7A

CONTINUES FROM FIG. 7A

. . .

```
# plot state-distributions by cluster
clus5.lab <- factor(anmc.clus5, labels=paste("Utilization Trajectory Cluster", 1:5))
seqdplot(anmc.seq, group=clus5.lab, border=NA)

# discern degree of pattern disorder between groups
# note: there is no significant relationship of entropy to position or first-injured body part
entropies <- seqient(anmc.seq)
lm.ent <- lm(entropies ~ CumLawEnf*AgeGrp, dsm_anmc_traminer)
summary(lm.ent)

# plot state-frequency for top 10 utilization patterns in order of frequency of pattern grouped
by age group
seqfplot(anmc.seq, weighted=TRUE, border=NA, withlegend="right", title="Weighted
frequencies", group=dsm_anmc_traminer$AgeGrp)

# plot representative trajectory sets grouped by age group
# using the default frequency criterion
seqrplot(anmc.seq, dist.matrix=anmc.om, group=dsm_anmc_traminer$AgeGrp, border=NA)

# plot complexity-sequence entropy-index (Theil's H) grouped by age group
seqplot(anmc.seq, type="Ht", group=dsm_anmc_traminer$AgeGrp, border=NA)

# plot mean-time in complexity states grouped by age group
seqmtplot(anmc.seq, group=dsm_anmc_traminer$AgeGrp, ylim=c(0, 30), border=NA)
# tabulate mean-time by complexity score by age group
by(anmc.seq, dsm_anmc_traminer$AgeGrp, seqmeant)

# calculate complexity A to complexity B transition rates for sequential states
anmc.trate <- seqtrate(anmc.seq)
round(anmc.trate, 3)

# calculate state frequencies by week
seqstatd(anmc.seq[,1:52])

# calculate medoid cluster sequences predicting characteristic patterns of complexity
medoid <- seqrep(anmc.seq, dist.matrix=anmc.om, criterion="dist", nrep=1)
print(medoid, format="SPS")
```

*FIG. 7B*

MINING OF SEQUENCES, BY DAY-IN-EPISODE (NOT ORDER)

EXAMPLE: (1) FIND SEQUENCES THAT OCCUR IN AT LEAST 10% OF 10,000 PATIENTS IN THIS VENU FOR THIS PERSCRIBER TYPE

```
> s3 <- cspade(t, parameter=list(support=0.10, maxwin=9))

set of 1260 sequences with most frequent items:
   47206    78903    15475    88925    67280   (Other)
     420      249      234      218      212     1695 most frequent elements:
 {47206}  {78903}  {15475}  {88925}  {67280}  (Other)
     346      244      229      214      208     1572 element (sequence) size distribution:
sizes
  1   2   3   4
 73 664 505  18 sequence length distribution:
lengths
  1   2   3   4   5
 51 548 560  97   4 summary of quality measures:
    support
 Min.   :0.1000
 1st Qu.:0.1110
 Median :0.1257
 Mean   :0.1468
 3rd Qu.:0.1549
 Max.   :0.7286 mining info:
 data ntransactions nsequences support
    t         90748      10000     0.1
```

(2) THEN MATCH TARGET PATIENT'S SEQUENCE TO THESE SEQUENCES IN ORDER TO SUGGEST WHAT BASKETS OF ORDERABLES ARE DOWNSTREAM

*FIG. 9*

United States Patent US 11,145,396 B1

DISCOVERING CONTEXT-SPECIFIC COMPLEXITY AND UTILIZATION SEQUENCES

CROSS-REFERENCE TO RELATED APPLICATIONS

This application is a divisional of U.S. application Ser. No. 14/281,593, filed on May 19, 2014, which claims the benefit of U.S. Provisional Application No. 61/824,377, filed on May 17, 2013; U.S. application Ser. No. 14/281,593 is a continuation in part application and claims the benefit of U.S. application Ser. No. 14/209,568, filed on Mar. 13, 2014, which is a continuation in part application and claims the benefit of U.S. application Ser. No. 14/175,750, filed on Feb. 7, 2014, which claims the benefit of U.S. Provisional Application No. 61/762,178, filed Feb. 7, 2013; each of which is hereby expressly incorporated by reference in its entirety.

INTRODUCTION

In many health care contexts, multiple comorbid conditions, including psychiatric or behavioral conditions, combine to produce a high likelihood of frequent utilization of health services. So called complex patients, such as patients considered to be complex cases or requiring complex care consume a disproportionate amount of services. In particular, one recent study indicates that ten percent of patients consume over sixty percent of health care resources. Moreover, these patients frequently do not achieve desirable outcomes, despite the level of services they utilize. In many instances, these patients do not adhere to prescribed regimens, which results in frequent returns with recurrence of patient condition or exacerbation of problems. Additionally, various factors may influence a patient's likelihood to follow a prescribed regimen or utilize a disproportionate level of health care services including concomitant mental health, substance abuse, unemployment, family issues, or other factors including socioeconomic complexity.

By way of illustration of an example of multiple comorbid conditions combining to produce a high likelihood of frequent utilization of health services, the epidemiology of heart failure has been the subject of many published research studies, but virtually all studies examine it in isolation from other conditions. To date, no one has investigated whether there are characteristic sequences of care episodes involving other conditions, such as arthritis pain or depression or dementia or other disabilities, nor has anyone investigated whether, if such sequences do exist, they are statistically associated with factors that might lead to meaningful, effective prevention of episodes of heart failure exacerbation. Partly, the lack of studies of this sort is due to the difficulty in examining sequences of events statistically. The statistical methods for measuring clusters of event sequences are only about 20 years old, and the methods are familiar to only a few people—virtually no one in medical disciplines.

Since it is well-known that patients with one or more comorbid conditions do run an increased risk of future health services utilization, it is de rigeur to suggest that the patient should receive some sort of preventive intervention. However, to date the preventive maneuvers are very non-specific and involve patient (re-)education, monitoring, performing general measures and temporizing ("watchful waiting"). The preventive maneuvers focus primarily on the chief complaint associated with the original condition and are agnostic about the interconnections between body systems and alterations in other concomitant conditions.

But in many conditions, significant patterns and interrelationships that manifest themselves over a period of time do exist. Specific preventive interventions that will be most effective in averting conditions that carry that increased risk, but to date it has not been practical to identify which patients should receive which case-management interventions. Addressing these questions requires discovering whether there are statistically significant trajectories of serial conditions—patterns for which context- or trajectory-specific preventive interventions might be designed. Based on the information these trajectories provide, patterns of patient utilization can be determined to predict future utilization, care-coordination interventions to effectively address and mitigate important prevalent patterns can be designed and implemented, and specific interventions that match a particular patient's pattern can be prescribed and implemented.

Accordingly, embodiments of the invention facilitate developing well-designed case-management and care-coordination programs to decrease inappropriate use of health care resources, reduce costs, and improve patient and caregiver understanding of disease process and symptom management. Increased patient and caregiver understanding of disease processes and symptom management and better prepare the patient or caregiver to manage the ongoing chronic conditions, which keeps the patient healthy, thereby avoiding the need for frequent acute interventions. In particular, the 30-day readmission rate for patients followed using transitional-care protocols can be decreased up to 4-fold.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. The present invention is defined by the claims.

Systems, methods, and computer-readable media are provided for case complexity and care complexity characterization, and for detecting matches of an individual patient's record with collections of other patients' records, with on serial, longitudinal patterns, referred to herein as time series "trajectories". For example, some embodiments facilitate the automatic, algorithm-guided ascertainment of record matches between (a) one patient's attributes and cumulative longitudinal pattern of serial conditions and (b) a plurality of other patients' longitudinal conditions records in a collection of online records that are stored in a computer system. In this way, embodiments may facilitate more efficient health services utilization, implementing programs to reduce case complexity and care complexity, preventive medicine, and risk management in health care.

In one aspect, time series are formed by (a) electronically representing and storing information pertaining to successive longitudinal episodes of health services utilization and the circumstances in which the episodes were incurred, (b) calculating time-series K-nearest-neighbor clusters and distances for each such combination, (c) determining the cluster to which a given candidate patient complexity record is nearest or belongs to, and (d) prescribing one or more interventions that are specific to the plurality of hazards that are characteristic of trajectories that are members of that cluster and that are deemed to be relevant to reducing or mitigating those hazards and thereby are efficacious in preventing adverse outcomes and subsequent excess utilization that are prevalent in that trajectory cluster.

BRIEF DESCRIPTION OF THE DRAWINGS

Embodiments are described in detail below with reference to the attached drawing figures, wherein:

FIGS. 5A and 5B illustratively depict example user interfaces for receiving patient information used for determining metrics for care complexity and case complexity;

FIG. 6A provides a depiction of time-series of patient condition complexity, by week, for a fifty-two-week window;

FIGS. 7A and 7B illustratively provide one example embodiment of a computer program routine for trajectory mining;

FIG. 9 illustratively presents an example of mining patent information from 10,000 to identify sequences matching a target patient's sequences for determining downstream baskets of patient orderables.

DETAILED DESCRIPTION

Figure 1A:
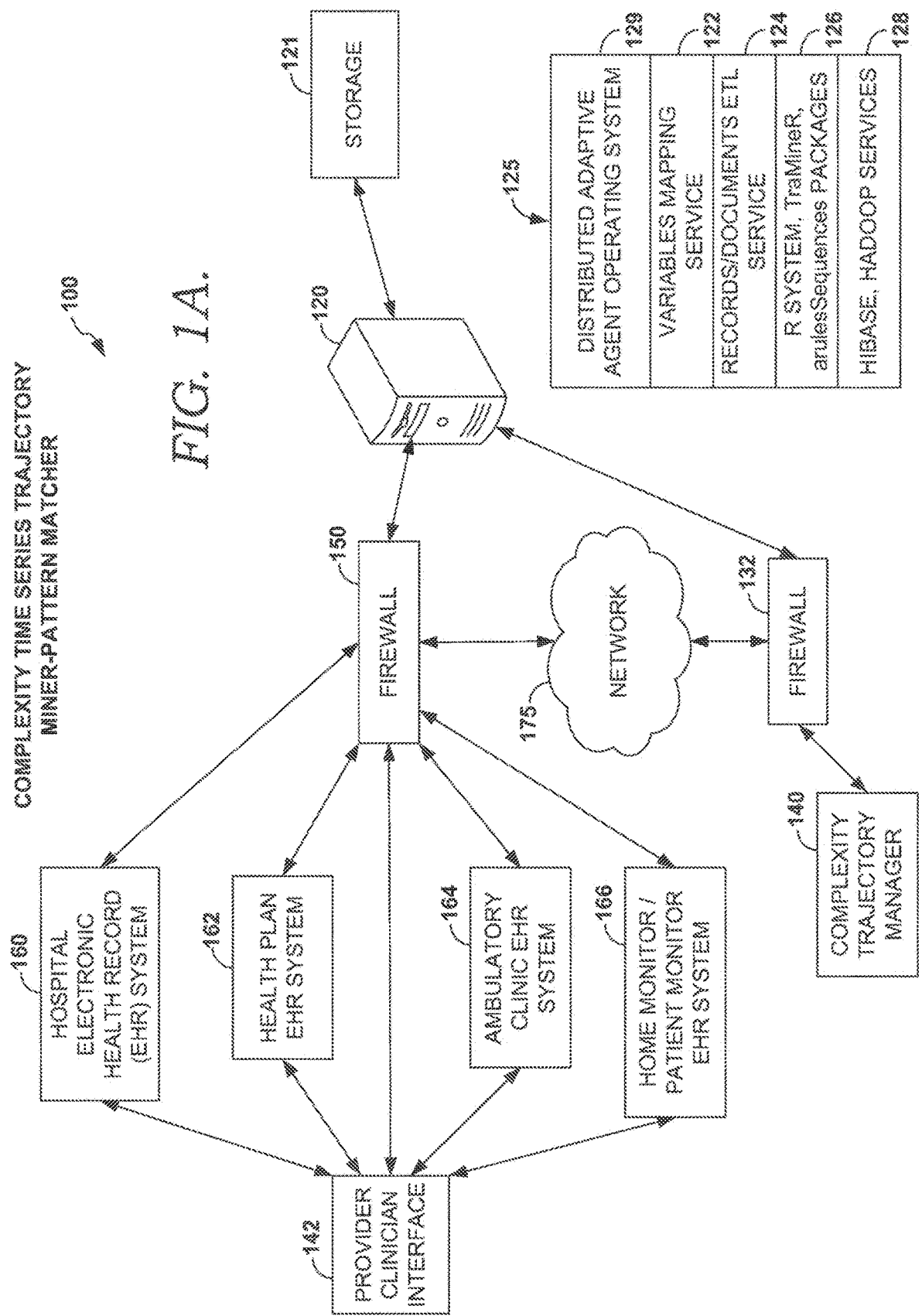
FIGS. 1A and 1B depict block diagrams of aspects of an exemplary operating environment suitable to implement embodiments of the present invention.

The subject matter of the present invention is described with specificity herein to meet statutory requirements. However, the description itself is not intended to limit the scope of this patent. Rather, the inventor has contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

As one skilled in the art will appreciate, embodiments of our invention may be embodied as, among other things: a method, system, or set of instructions embodied on one or more computer-readable media. Accordingly, the embodiments may take the form of a hardware embodiment, a software embodiment, or an embodiment combining software and hardware. In one embodiment, the invention takes the form of a computer-program product that includes computer-usable instructions embodied on one or more computer-readable media.

Computer-readable media include both volatile and nonvolatile media, removable nonremovable media, and contemplate media readable by a database, a switch, and various other network devices. By way of example, and not limitation, computer-readable media comprise media implemented in any method or technology for storing information, including computer-storage media and communications media. Examples of stored information include computer-useable instructions, data structures, program modules, and other data representations. Computer storage media examples include, but are not limited to information-delivery media, RAM, ROM, EEPROM, flash memory or other memory technology, CD-ROM, digital versatile discs (DVD), holographic media or other optical disc storage, magnetic cassettes, magnetic tape, magnetic disk storage, other magnetic storage devices, and other storage devices. These technologies can store data momentarily, temporarily, or permanently.

Embodiments of the invention are directed to methods, computer systems, and computer-readable media for patient case complexity and care complexity characterization, and for detecting matches of an individual patient's record with collections of other patients' records, based on serial, longitudinal patterns (time series "trajectories").

Other attempts or efforts at characterizing patient condition are deficient due to: (1) excessive false-negative error rate (including false misses, and consequent failure to allocate case-management and care-coordination services optimally), associated with neglecting time series information regarding serial sequences or trajectories of multiple conditions sustained over a period of time; (2) excessive false-positive error rate (false hits), commonly arising due to consideration only of individual conditions or other attributes and neglecting distinguishing features contained in time series information; and (3) failure to take into account empirical associations or causative relationships between one or more conditions or disease processes and (a) the physiology of coupled systems and (b) compensatory physiological or psychological effects on the coupled systems during treatment.

Additional shortcomings include an over emphasis primarily on the number of comorbid medical diagnoses, which has only weak statistical correlation with utilization intensity and severity. In particular, constellations of multiple diagnoses are not necessarily complex in terms of diagnostic and therapeutic processes. Furthermore, often some medical diagnoses are not even recorded. Additionally still, other attempts fail to consider regimen-adherence complexity from a patient's and caregivers' perspective, care plan implementation complexity from a nurse's or caregiver's perspective, and complexity that is manifested by longitudinal sequences of serial care episodes.

Accordingly, it is therefore highly valuable and highly desirable to provide embodiments of the methods and systems described herein, for longitudinal patient condition (including multi-condition) trajectory classification that takes advantage of time-oriented information, such as information that is readily available for each of the records in a repository and for any new record for which a match in the repository is sought.

Moreover, while a considerable number of studies have described the incidence and condition pattern (condition type and severity), much less is known about risk factors or acute-care episode causative mechanisms. Some players experience only one or a few serial acute-care episodes per year, while other patients experience a large number of serial episodes. Some patients experience exacerbations whose duration is short even if the episodes arise frequently, and these patients accumulate relatively little time each year consuming health services. By contrast, other patients experience complex constellations of multiple conditions whose resolution takes a long time, or whose non-adherence to the prescribed regimen results in episodic deterioration requiring acute management, or which confer chronic vulnerability due to socioeconomic or psychiatric condition resulting in their periodically accessing the health system with a frequency that is disproportionate with their medical severity. All of these give rise to distinctive patterns of repeated utilization of health services.

Accordingly, some embodiments of the present invention comprise statistical and computational systems and methods for inferring clusters of similar sequences or trajectories of serial conditions and for matching individual patient's patterns to patterns represented by cluster members based on nearest-neighbor trajectory distances and trajectory disorder ("entropy index") values.

In some aspects, sequence or trajectory cluster discovery can considered as statistical association discovery over a temporal database. While association rules discover only intra-event patterns (called frequent itemsets), we now also have to discover inter-event patterns (called frequent sequences or trajectories).

Various algorithms considered for mining sequential pattern information are unable to scale well with increasing sequence length and database size. The search space is extremely large. For example, with m attributes there are $O(m^k)$ potentially frequent sequences of length k. With hundreds to many thousands (or millions, depending on the context) of objects in a database, the problem of I/O minimization becomes paramount. Algorithms that are iterative in nature would require as many full database scans as the longest time series sequence.

Turning now to FIG. 1A there is presented an example operating environment 100 suitable for practicing embodiments of the invention. Example operating environment 100 includes a computerized system for compiling and running an embodiment of a patient condition characterization decision support recommendation service. With reference to FIG. 1A, one or more electronic health record (EHR) systems such as hospital EHR system 160, ambulatory clinic EHR system 164, Health Plan EHR system 162, and Home Monitor/Patient Monitor EHR system 166 are communicatively coupled to network 175, behind a firewall 150, which is communicatively coupled to computer system 120. In embodiments, network 175 includes the Internet, a public network, a private network, or similar communications network.

Operating environment 100 also includes a firewall 132 between complexity trajectory manager 140, computer system 120, and network 175. Although environment 100 includes firewalls 150 and 132, it is contemplated that some operating environments may not have firewalls. In embodiments having a firewall, the firewall may reside on a component between the component and network 175, such as on a server (not shown) or may reside on or as part of the component. Thus, in some embodiments, firewall 150 or 132 may comprise a separate firewall associated with each component (or some components) shown communicatively coupled to the firewall.

Embodiments of electronic health record (EHR) systems 160, 162, 164, and 166 include one or more data stores of health records, such as data store 121, and may further include one or more computers or servers that facilitate the storing and retrieval of the health records. Firewall 150 may comprise a separate firewall associated with each EHR system, in some embodiments. Furthermore, in some embodiments, one or more EHR systems 160, 162, 164, and 166 may be implemented as a cloud-based platform or may be distributed across multiple physical locations. In some embodiments, EHR systems 160, 162, 164, and 166 further include record systems which store real-time or near real-time patient information, such as wearable, bedside, or in-home patient monitors, for example. For example, in some embodiments, monitor EHR system 166 comprises a sensor component such as a patient-wearable sensor component or sensor component integrated into the patient's living environment. Examples of sensor components of monitor EHR 166 include wherein the sensor is attached to the patient clothing, worn around the patient's neck, leg, arm, wrist, ankle, etc., skin-patch sensor, ingestible or subdermal sensor, or wherein sensor component(s) are integrated into the patient's living environment (including the bed or bathroom), sensors operable with or through a smart phone carried by the patient, for example. Embodiments of monitor EHR system 166 may store patient data locally or communicate data over network 175 to be stored remotely.

Example operating environment 100 further includes provider clinician interface 142 communicatively coupled to the one or more EHRs 160, 162, 164, and 166. Embodiments of interface 142 may take the form of a user interface operated by a software application or set of applications on a client computing device such as a personal computer, laptop, smartphone, or tablet computing device. In one embodiment, the application includes the PowerChart® software, manufactured by Cerner Corporation. In one embodiment, the application is a Web-based application or applet. Provider clinician application facilitates accessing and receiving information from a user or health care provider about a specific patient or set of patients for which characterization is to be performed and facilitates the display of results, recommendations or orders, for example. In some embodiments interface 142 also facilitates receiving orders for the patient from the clinician/user, based on the results. For example, interface 142 might display results to a user indicating that a given patient is significantly more likely to suffer a particular condition or utilize particular health services, given a previously occurring condition, pattern of conditions, patient history, or other factors, and based on that patient's age, history, or other demographic, display recommendations for patient treatment or facilitate receiving instructions for care.

Example operating environment 100 further includes computer system 120, which may take the form of a server, which is communicatively coupled through firewall 150 to EHR systems 160, 162, 164, and 166, and also through firewall 132 to complexity trajectory manager 140.

Computer system 120 comprises one or more processors operable to receive instructions and process them accordingly, and may be embodied as a single computing device or multiple computing devices communicatively coupled to each other. In one embodiment, processing actions performed by system 120 are distributed among multiple locations such as a local client and one or more remote servers. In one embodiment, system 120 comprises one or more computing devices, such as a server, desktop computer, laptop, or tablet, cloud-computing device or distributed computing architecture, a portable computing device such as a laptop, tablet, ultra-mobile P.C., or a mobile phone.

In embodiments, complexity trajectory manager 140 may take the form of a software application operating on one or more mobile computing devices, tablets, smart-phones, front-end terminals in communication with back-end computing systems, laptops or other computing devices. In some embodiments, complexity trajectory manager 140 includes a Web-based application or collection of applications that is usable to manage services provided by embodiments of the invention. In some embodiments, manager 140 facilitates calibration, evaluation, re-testing or tailoring, and in some embodiments, manager 140 facilitates receiving feedback information.

Embodiments of computer system 120 include computer software stack 125, which in some embodiments operates in the cloud, as a distributed system on a virtualization layer within computer system 120. Some embodiments of software stack 125 include a distributed adaptive agent operating system 129, which may be implemented as a platform in the cloud, and which is capable of hosting a number of services such as 122, 124, 126, and 128. Embodiments of services 122, 124, 126, and 128 run as a local or distributed stack in the cloud, on one or more personal computers or servers such as 120, and/or a computing device running manager 140. In one embodiment, manager 140 operates in conjunction with software stack 125.

In embodiments, variables mapping service 122 and records/documents ETL service 124 provide services that facilitate retrieving frequent itemsets, extracting database records, and cleaning the values of variables in records. For example, variables mapping service 122 may perform functions for synonymic discovery or mapping disparate health systems' ontologies, such as determining that a particular medication frequency of a first record system is the same as another record system. In some embodiments, these services invoke software services 126. Software services 126 perform statistical software operations, and include statistical calculation packages such as, in one embodiment, the R system (the R-project for Statistical Computing, which supports R-packages or modules tailored for specific statistical operations, and which is accessible through the Comprehensive R Archive Network (CRAN) at http://cran.r-project.org); R-system modules or packages including TraMineR or similar services for facilitating trajectory mining, and arulesSequences or similar services for facilitating operations such as K-nearest neighbor distance calculations. Software packages 126 are associated with services 128, which include Apache Hadoop and Hbase framework, or similar frameworks operable for providing a distributed file system, and which in some embodiments facilitate provide access to cloud-based services such as those provided by Cerner Healthe Intent®.

Example operating environment 100 also includes data store 121, which in some embodiments includes patient data for a candidate patient and information for multiple patients; variables associated with patient recommendations; recommendation knowledge base; recommendation rules; recommendations; recommendation update statistics; an operational data store, which stores events, frequent itemsets (such as "X often happens with Y", for example), and item sets index information; association rulebases; agent libraries, solvers and solver libraries, and other similar information including data and computer-usable instructions; patient-derived data; and health care provider information, for example. In some embodiments, data store 121 comprises the data stores associated with the one or more EHR systems, such as 161, 162, 164, and 166 and complexity trajectory manager 140. Further, although depicted as a single data store, data store 121 may comprise one or more data stores, or may be in the cloud.

Figure 1B:
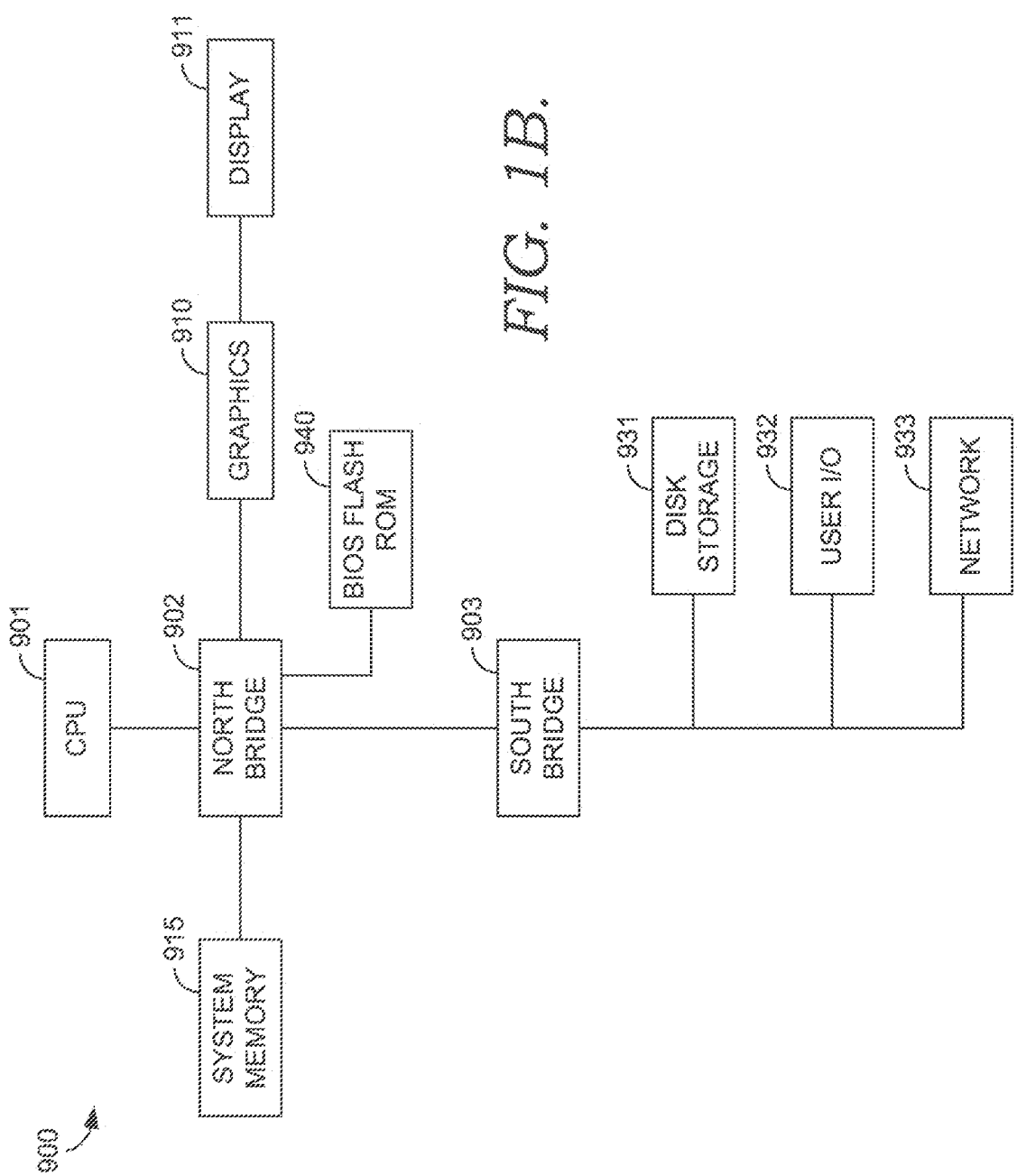

Turning briefly to FIG. 1B, there is shown one example embodiment of computing system 900 that has software instructions for storage of data and programs in computer-readable media. Computing system 900 is representative of a system architecture that is suitable for computer systems such as computing system 120. One or more CPUs such as 901, have internal memory for storage and couple to the north bridge device 902, allowing CPU 901 to store instructions and data elements in system memory 915, or memory associated with graphics card 910, which is coupled to display 911. Bios flash ROM 940 couples to north bridge device 902. South bridge device 903 connects to north Bridge device 902 allowing CPU 901 to store instructions and data elements in disk storage 931 such as a fixed disk or USB disk, or to make use of network 933 for remote storage. User I/O device 932 such as a communication device, a mouse, a touch screen, a joystick, a touch stick, a trackball, or keyboard, couples to CPU 901 through south bridge 903 as well. The system architecture depicted in FIG. 1B is provided as one example of any number of suitable computer architectures, such as computing architectures that support local, distributed, or cloud-based software platforms, and are suitable for supporting computing system 120.

Returning to FIG. 1A, in some embodiments, computer system 120 is a computing system made up of one or more computing devices. In an embodiment, computer system 120 includes an adaptive multi-agent operating system, but it will be appreciated that computer system 120 may also take the form of an adaptive single agent system or a non-agent system. Computer system 120 may be a distributed computing system, a data processing system, a centralized computing system, a single computer such as a desktop or laptop computer or a networked computing system.

In some embodiments, computer system 120 is a multi-agent computer system with agents. A multi-agent system may be used to address the issues of distributed intelligence and interaction by providing the capability to design and implement complex applications using formal modeling to solve complex problems and divide and conquer these problem spaces. Whereas object-oriented systems comprise objects communicating with other objects using procedural messaging, agent-oriented systems use agents based on beliefs, capabilities and choices that communicate via declarative messaging and use abstractions to allow for future adaptations and flexibility. An agent has its own thread of control which promotes the concept of autonomy. Additional information about the capabilities and functionality of agents and distributed multi-agent operating systems, as they relate to these embodiments, is provided in U.S. patent application Ser. No. 13/250,072, filed on Sep. 30, 2011, which is herein incorporated by reference in its entirety.

Figure 2:
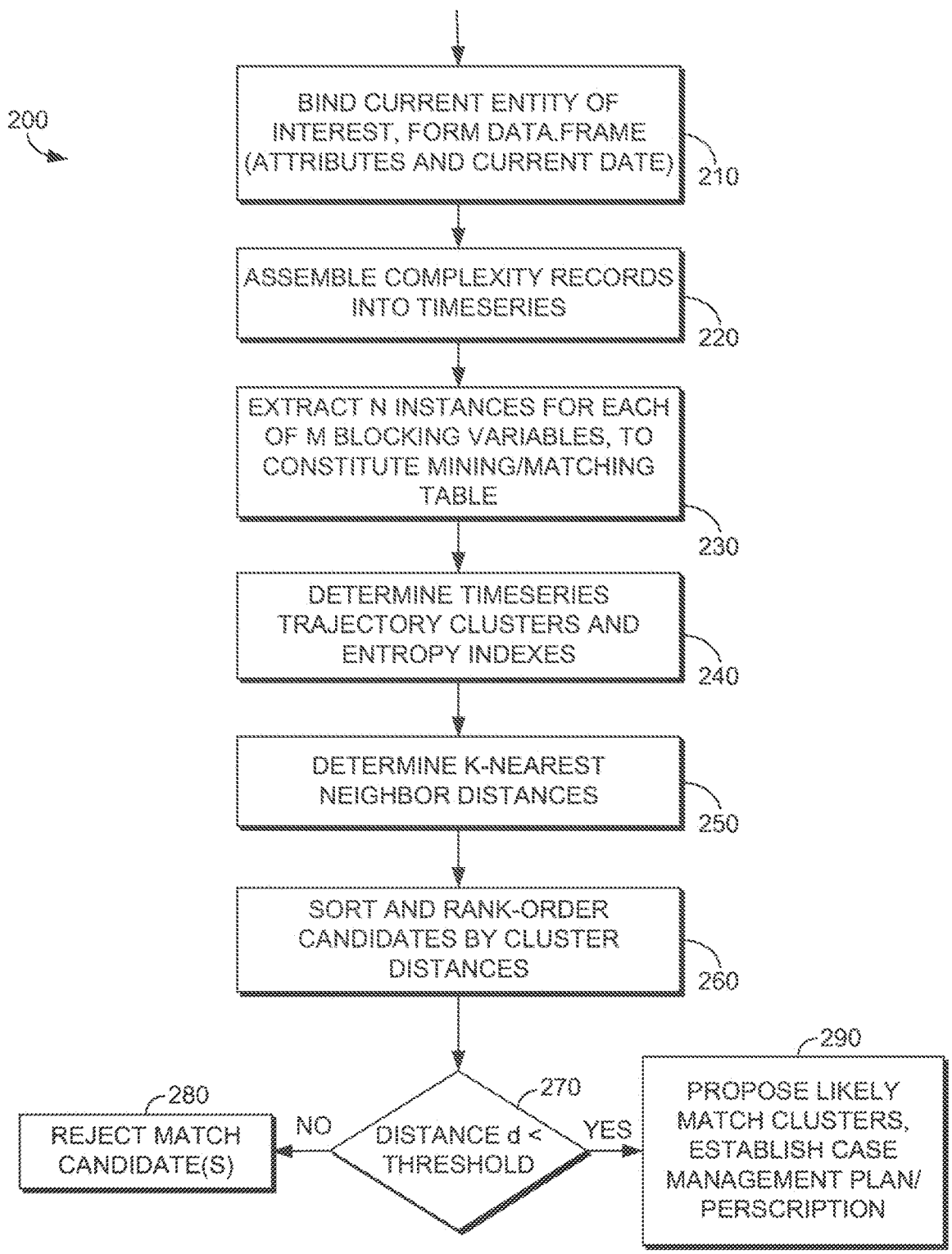
FIG. 2 depicts a flow diagram of a method for characterizing patient condition, in accordance with an embodiments of the present invention.

Turning now to FIG. 2, a flow diagram is provided for an embodiment of a method for patient condition characterization and detecting matches of an individual patient's record with collections of other patients' records having serial, time series trajectories, and referred to generally herein as method 200. A trajectory implies a potential change or potential longitudinal alteration from one condition or state of a property to another condition, and may be viewed as a longitudinal sequence of states. Accordingly, an objective in some embodiments is to compare a first patient's attributes and longitudinal patterns against other patients' attributes and longitudinal patterns in order to determine a cluster(s) in which the first patient attributes and longitudinal patterns best fit.

With reference to FIG. 2, some embodiments of the invention use a vertical identification-list ("id-list") database format, wherein associated with each sequence are a list of patients in whom the sequence occurs, along with corresponding time-stamps. In these embodiments, all frequent sequences can be enumerated via simple temporal joins (or intersections) on id-lists. Additionally, some embodiments use a sparse-matrix approach to decompose the original search space (lattice) into smaller pieces (sub-lattices) which can then be processed independently, either in main-memory on a single processor or in distributed memory on multiple parallel processors. In this manner, embodiments previously requiring three database scans, require only a single scan with some pre-processed information, thus minimizing I/O costs. In some embodiments, the problem decomposition is decoupled from the pattern search. Thus some embodiments utilize two different search strategies for enumerating the frequent sequences within each sublattice: breadth-first and depth-first search, according to algorithms that are already known to those practiced in the art.

At a step 210 of method 200, bind the current entity of interest. In embodiments, the entity of interest is the entity for which it is desired to find other matching entities in a target system. For example, the entity of interest may represent the condition or health record(s) of person or object for which candidate matches are sought, such as an individual patient or a set (plurality) of patients. In embodiments, information specifying a patient or set of patients may be received from a user such as carried out by a clinician, health care provider, trainer, or manager, or received from a computer program, such as from a software agent or software routine. In some embodiments, a batch process is used to identify the patient or set of patients. In some embodiments, step 210 includes identifying attributes and date information associated with the entity of interest, such as for example, age, information about specific acute-care episodes including condition type(s), date of first acute-care episode, date(s) of subsequent acute-care episodes, care services utilized in acute-care episodes, durations of adduce-care episodes, current date, other EHR information, and other attributes that may be used for determining a trajectory cluster. Further, in some embodiments, the information of step 210 is formed into a data.frame, which is a special data type in the R-system that may include embedded arrays.

At a step 220, the records such as patient condition/acute-care episode records or other patient case-complexity or care-complexity records are assembled into a timeseries format. In some embodiments, this includes patient condition or care service utilization records and other factors such various attributes identified in step 210. An illustrative depiction of example timeseries determined in step 220 is provided in FIG. 6A. In some embodiments, the records, date, and patient attribute information (or factors) are assembled into R-system data.frame data types. So for example, patient-condition records comprising a 52-long row vector, such as shown in FIG. 6A, would be a component of a data.frame.

Turning briefly to FIG. 6A, an illustrative chart of time-series of patient-condition complexity, by week for a multi-week window (in this example, a 52-week moving window), is provided and referred to generally as 600. Each row of chart 600 corresponds to a patient; each column w.01 through w.52 (not shown) corresponds to a week of time. Shaded or colored cells indicate complexity of particular patient condition(s) or acute-care episode(s) for that patient during that week. In this particular example illustration of the timeseries information, the patient information represents de-identified player data from approximately 300 representative cases over a 1-year (52-week) interval. As shown, most of these patients experience from at least one acute-care episode per year, but many have more than one acute-care episode, which may result from or be worsened by the first acute-care episode.

Each entry per week, in columns w.01 through w.02 includes a value that corresponds to patient care complexity or patient case complexity for that time period (here, 1 week). In some embodiments, this value represents a complexity score based on a metric for determining the level of patient care or case complexity for that time period. In some embodiments, the complexity score is a composite score, which comprises a plurality of metrics for measuring patient care or patient case complexity. For example, in an embodiment, the complexity score comprises composite score, wherein the composite score includes a measure of drug complexity, such as provided by the Kelly medication complexity index (MCI), and further includes a measure of patient care complexity, such as provided by the care complexity prediction instrument (COMPRI). In an embodiment, the composite score is embodied as a 1-byte hexadecimal number (00 to FF), wherein the lower nybble represents the MCI score and the upper nybble represents the COMPRI. In some embodiments, the composite score further includes a measure of procedural complexity for patient treatment. For example, a patient that is required to take 6 baths per day may be determined to have a high procedural complexity score. In some of these embodiments, the composite score may thus be a multi-byte score.

The values for the COMPRI, MCI, or other complexity metrics may be determined automatically such as by a software routine or agent, by user such as a caregiver, family member, or patient, or combination of software and user. Turning briefly to FIGS. 5A and 5B, example user interfaces are provided for receiving patient information used for determining metrics for care complexity and case complexity. In particular, FIG. 5A shows an example user interface 800 for receiving information used for determining a COMPRI score; and FIG. 5B shows an example user interface 850 for receiving information used for determining an MCI score, which may be per patient or per medication administered to the patient. In some embodiments, user interfaces 800 and 850 are used on provider clinician interface 142, of FIG. 1A. In some embodiments software routines or software agents facilitate retrieving at least some of the information in the fields of these interfaces, such as the additional information from EHR of user interface 800. In these embodiments, the software agent or routine may auto-populate these fields with the retrieved information. In some embodiments, the "data complete" field of interface 800 and 850 provides feedback to the user indicating either that all of the information has been provided (YES) or that there are fields in which information is missing or incorrectly presented (such as a number or letter other than Y/N entered into a field requiring only a "Y" or "N").

Figure 6B:
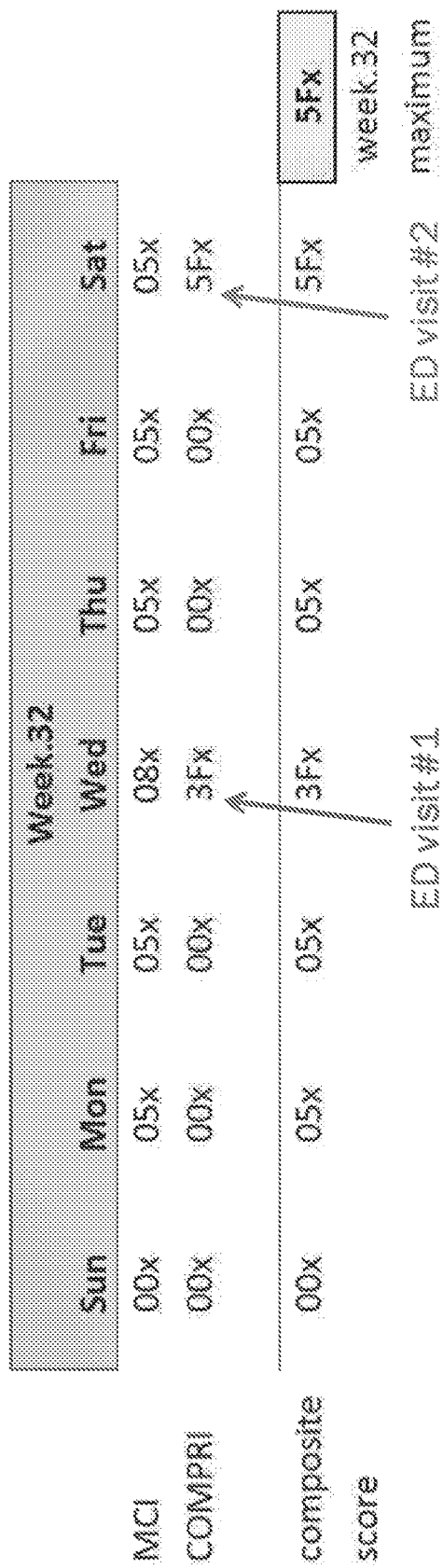
FIG. 6B depicts an example of determining a complexity composite score weekly maxima.

As described above, in some embodiments, patient condition complexity is determined over a period of time, such as 1 week, and represented as a complexity score. FIG. 6B shows an example of determining complexity composite scores for each time period (here, 1 week) based on the MCI and COMPRI scores for a particular patient. The example of FIG. 6B corresponds to patient condition episodes transpiring over a week (here, the thirty-second week as indicated by "week.32"). As described above, in this example embodiment, the complexity score, expressed as a hexadecimal value, ranges from 00 to FF (255 in decimal notation), such that the lower significant nybble represents the MCI score and the upper significant nybble is the COMPRI. In some embodiments, such as this example embodiment, the score is segmented with a 32-level quantization such that the lower part of the COMPRI is always all ones (Fx). Thus if an unscheduled acute-care episode occurs during the time period, it always overrides whatever peri-episode ambulatory medication complexity would have prevailed. More specifically, in some embodiments, a bitwise OR operation is carried out between the MCI and COMPRI scores. Since the lower nybble for the MCI score is all ones, if it is OR'd with anything else, it will always override other values.

Continuing with the example of FIG. 6B, on Sunday nothing happens. Thus the MCI and COMPRI scores for Sunday are each zero (represented as a hexadecimal, 1-nybble value as "00x"). The composite complexity score for Sunday is thus zero as well. On Monday, the patient is prescribed a series of medications, which is indicated as an MCI score of 05x on Monday. The composite complexity score for Monday is thus 05x. On Wednesday, the patient has a first emergency department (ED) visit resulting in a COMPRI score of 3Fx; on that same date the patient is prescribed medications corresponding to a complexity score of 08x. This is more complex than the previous drug regimen having corresponding complexity score 05x, resulting from Monday's prescription. The composite complexity score for Wednesday is 3Fx. On Saturday the patient has a second ED visit, which is more complex than the first visit, as indicated by the COMPRI score of 5Fx.

In this example, each day is assigned a complexity score, and a maximum score is determined for the week. In some situations, a score may be assigned for a shorter or longer time period. For example, the maximum complexity score may be determined over a day or over an episode such as a hospital stay. In some embodiments, the score may be generated multiple times per day, such as where there are multiple episodes within a 24 hour period. In such situations, the score may be consolidated, in some embodiments, into a single score corresponding to the worst (or most complex) degree of care. In some embodiments, the number of episodes is considered when scoring the complexity, such that multiple episodes of the same complexity over a time period will result in a higher complexity score than only a single episode of the same complexity over the same time period. In some embodiments, scores for certain time periods, such as weekends, may be weighted differently than scores for other time periods.

In this embodiment, a weekly maxima composite complexity score is determined (here the weekly maximum is 5Fx, which was the score from Saturday). In some embodiments, a software routine such as a batch process or software agent determines the maxima over each week or time period. In some embodiments, this score is then posted to the patients EHR or made available to other health care services. For example, in some embodiments, the scores may be stored in data store 121 and made accessible method 200.

Accordingly, in this example embodiment, each week is evaluated to determine a maximum complexity score (determined to be "5Fx" in FIG. 6B). The complexity score for each week (or time period) over the course of a window of time periods (such as the 52 week moving window of FIG. 6A) forms the time series for the patient. Therefore, returning to the example shown in FIG. 6A, which shows time series of patient condition complexity, for columns w.01 through w.52, each entry represents composite complexity score for that patient, for that week.

Continuing with FIG. 6A, the left-hand side of chart 600 shows a patient ID, and example patient attributes or factors, which may be used in step 220 of method 200. Example attributes or factors include age (or age group), number of comorbid medical diagnoses, whether the patient is on Medicaid/SSI, cumulative law enforcement history over a period of time, such as 10 years. In other embodiments this information may include other patient demographic data, socioeconomic status or metrics, cultural information about the patient, location where patient resides, alcohol/drug use and medication history, habits or other user behaviors including risky behaviors, employment status, income, or other information that may be used to characterize patients. Some embodiments merely consider trajectories of patient case or care complexity and do not use or require information such as shown on the left-hand side of FIG. 6A.

Turning back to FIG. 2 and continuing with step 220, timeseries are thus assembled. In some embodiments, timeseries may assembled and used for each of however many patient attributes, conditions, or patient patterns, are desired to be examined, as described in the next step. At a step 230, for each M blocking variables, N instances are extracted to constitute a candidate trajectory mining/matching table, where M and N are integers greater than or equal to zero. In embodiments, step 230 includes selecting or identifying one or more independent demographic variables that are present in both a reference system and the target system associated with each entity, that are to be used as 'blocking' variables. Blocking variables can include variables such as age, first acute-care episode, or other patient factors (such as described above), or may also include variables in a specific context, such as whether the patient has other specific conditions, for example. Thus one example may include variables indicating patients on Medicaid/SSI who have diabetes or variables corresponding to patients less than 17 years of age with asthma, where a blocking variable might indicate a specific forced expiratory volume in 1 sec. In some embodiments, blocking variables may be used to determine how data sets are retrieved, when dealing with large-demographic data sets. Continuing with step 230, in some embodiments, from the target system, database records are extracted which contain lexically similar values for the selected blocking variables' values. In embodiments, the extraction is based on factors or attributes identified in step 210. Put another way, filter criteria for the extraction includes the entity of interest and the attributes of the entity that are of interest. In some embodiments, this is facilitated using a hash table to establish the degree of similarity for retrieval. In some embodiments, In some embodiments, for each entity retrieved from the extraction, extract the date-time coordinates for the episodes that the retrieved records represent; compute inter-episode time intervals that separate the records in time; and assemble the intervals as time series associated with each record. In some embodiments, this time series comprises elements representing the time interval between episodes. For example, a simple time series might include numbers representing the number of weeks, days, or hours between episodes.

At a step 240, timeseries trajectory clusters are determined. In embodiments, timeseries trajectory clusters are computes using software services 126 of FIG. 1A, such as the TraMineR package. One example embodiment of a computer program routine for trajectory mining is illustratively provided in FIGS. 7A and 7B. A trajectory-mining statistical algorithm as implemented by software services 126, such as the example embodiment shown in FIGS. 7A and 7B, can automatically and discover certain 'clusters' of trajectories that are quantitatively prevalent or frequent enough to characterize the acute-care episode patterns and transitions from one condition episode to subsequent condition episodes. Embodiments of step 240 may produce stable clusters or subsets of clusters, which demographically, in terms of entity specification, have similar longitudinal sequence of states. Thus in some embodiments, step 240 comprises computing a multi-cluster math model and extracting cluster assignment from model results for each entity of interest. An illustrative example of clusters generated by step 240 is provided in FIG. 3, which is described below.

In some embodiments, step 240 may also determine entropy indexes. Illustrative examples of entropy indexes are provided in FIG. 4. In some embodiments, software services 126, such as the TraMineR package output optionally individual or summary statistics or a timeseries from which a clinician or caregiver might look at slopes, rates of change, accelerations, or other properties.

Figure 4:
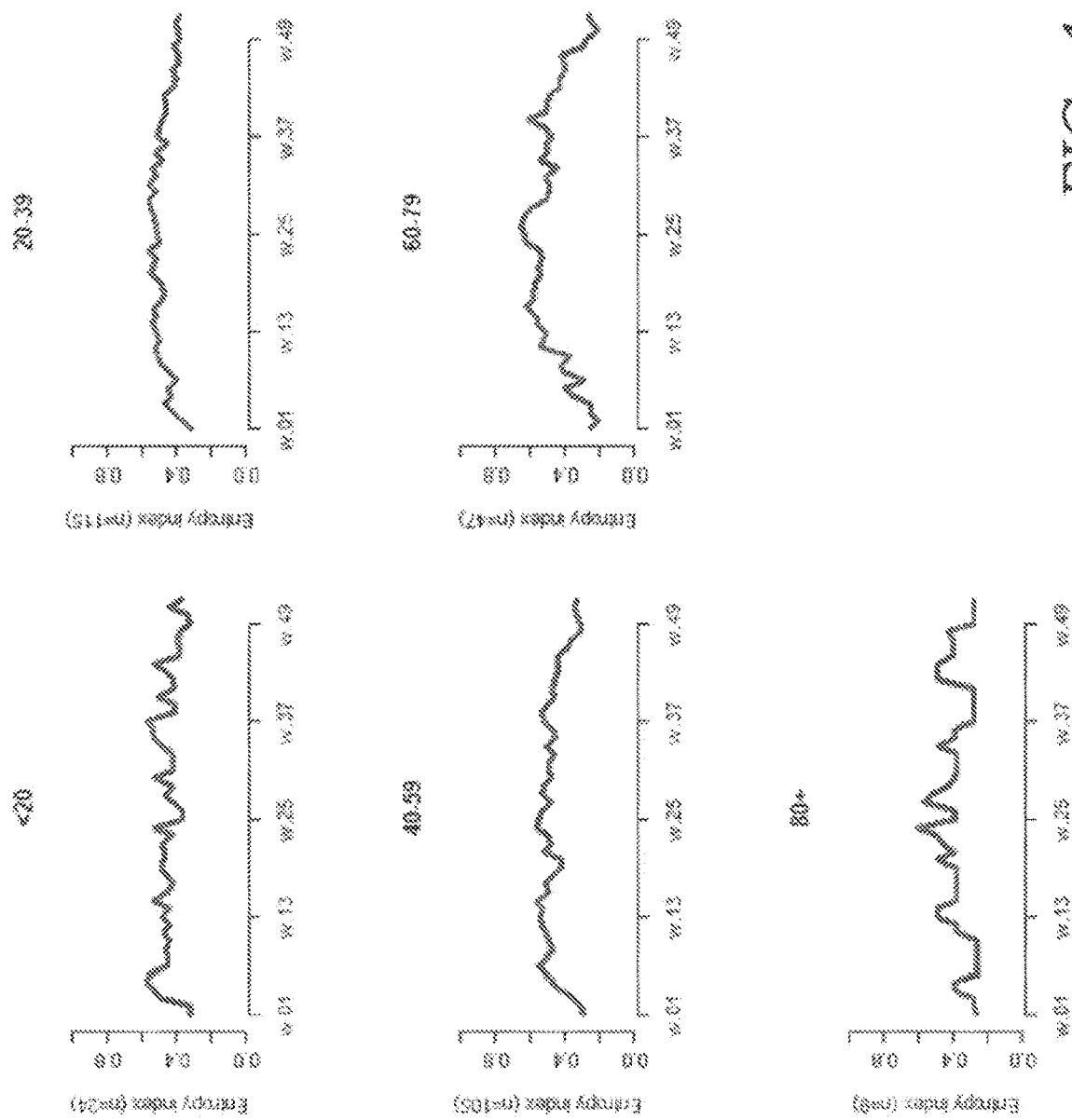
FIG. 4 depicts entropy indices of patient-condition trajectories, determined by age-group.

With reference to FIG. 4, entropy information such as presented herein enables a caregiver or clinician to see the complexity and amount of chaos for a particular case. In some embodiments, entropy information may be presented to a user, such as a clinician or caregiver, via interface 142 of FIG. 1A. In some embodiments, this information may be used for managing resources or taking action such as prescribing other treatments, based on the entropy. In particular, the disruption or chaos measured by entropy provides a valuable indicator for program management, health services, and provisioning. It is important to the accountable-care organizations to be able to figure out what is causing particular disruptions (or chaos) and then to design program changes to mitigate that, since the degree of chaos may be indicative of wasting their precious resources.

Accordingly, some embodiments of the invention include systems, methods, and computer-readable media for facilitating clinical decision making by determining the entropy level and evaluating the entropy level for a particular case. In some embodiments, based on the determined entropy level, specific treatments may be recommended for the patient. In some embodiments, based on the determined entropy level, the patient may be classified as belonging to a particular class for purposes of administering insurance and health care resources. In some embodiments, changes in entropy levels may be used for evaluating the effectiveness of a particular program or health care institution.

As shown in FIG. 4, entropy levels are clustered by patient age-range. Patients less than 20 years old (top left-hand side) and between 20-39 years old (top right-hand side) exhibit a comparatively constant entropy ('disorder', randomness) in their patterns of acute-care episodes through the year. For the example data shown, for the 20-39 year olds, their condition sequences have trajectory entropy values that stay relatively the same around H=0.4. Patients ages 60-79 (middle right-hand side) have slightly less variability in their acute-care episode sequences early in the year and later in the year, and peak at about H=0.6 in the middle of the year.

Returning to FIG. 2, at a step 250, in some embodiments, K-nearest neighbor distance calculations are determined. This optional step facilitates identifying the boundaries of the clusters. In some embodiments, this step includes taking the date-time coordinates associated with a candidate record to be matched and computing for each retrieved record the cluster distance that separates the candidate record from the centroid coordinates of the nearest trajectory cluster. In some embodiments, this step is performed using software services 126 of FIG. 1A, such as the open-source arulesSequences package.

In embodiments this step can be viewed as looking for proximity to the clusters produced in step 240 based on multiple variables. A centroid is associated with the clusters (such as those illustratively depicted in FIG. 3), in the multi-dimensional vector space, about which the distance of a particular member of that cluster may be characterized. In some embodiments, for each of the "rows" or timeseries, such as shown in FIG. 6A, the arulesSequences software package returns an array with a cluster identification.

At a step 260, in some embodiments, candidate matches are sorted and ranked by cluster distances. This optional step facilitates the comparison of step 270 by reducing the number of comparisons, because, for a rank-ordered set of candidate matches, comparisons may be performed in order until candidate matches satisfy or fail the threshold comparison.

At a step 270, determine for the entity whether the distance d exceeds a threshold. In some embodiments, the threshold is an heuristic threshold. In some embodiments, the use case associated with the potential match is used to determine the threshold. For example, in a certain uses such as for broad populations, a lower threshold may be appropriate, but for an individual patient, a higher threshold may be used. In some embodiments, a care provider or clinician may set the threshold; the threshold may be set from a table of associated use-cases; or the threshold may be set based on the determined distances, for example, where there is a gap between successive rank-ordered cluster distances. In some embodiments, an agent of a multi-agent computer system, such as computer system 120 of FIG. 1A, is used to determine the threshold.

At a step 280, where the distance does not satisfy the threshold, then the entity is rejected as an improbably match that should not be linked with the candidate record. On the other hand, if for a given entity the distance is less than the threshold, then at a step 290, that cluster is indicated as a probable match for the candidate record. In some embodiments, these matches are reported to a clinician or caregiver, and may be reported as results displayed on interface 142 of FIG. 1A. In embodiments, the probable matches determined in step 280 merit consideration for preventive intervention that is well-suited to mitigating the serial-condition trajectory risks that are associated with members of that cluster.

Figure 3:
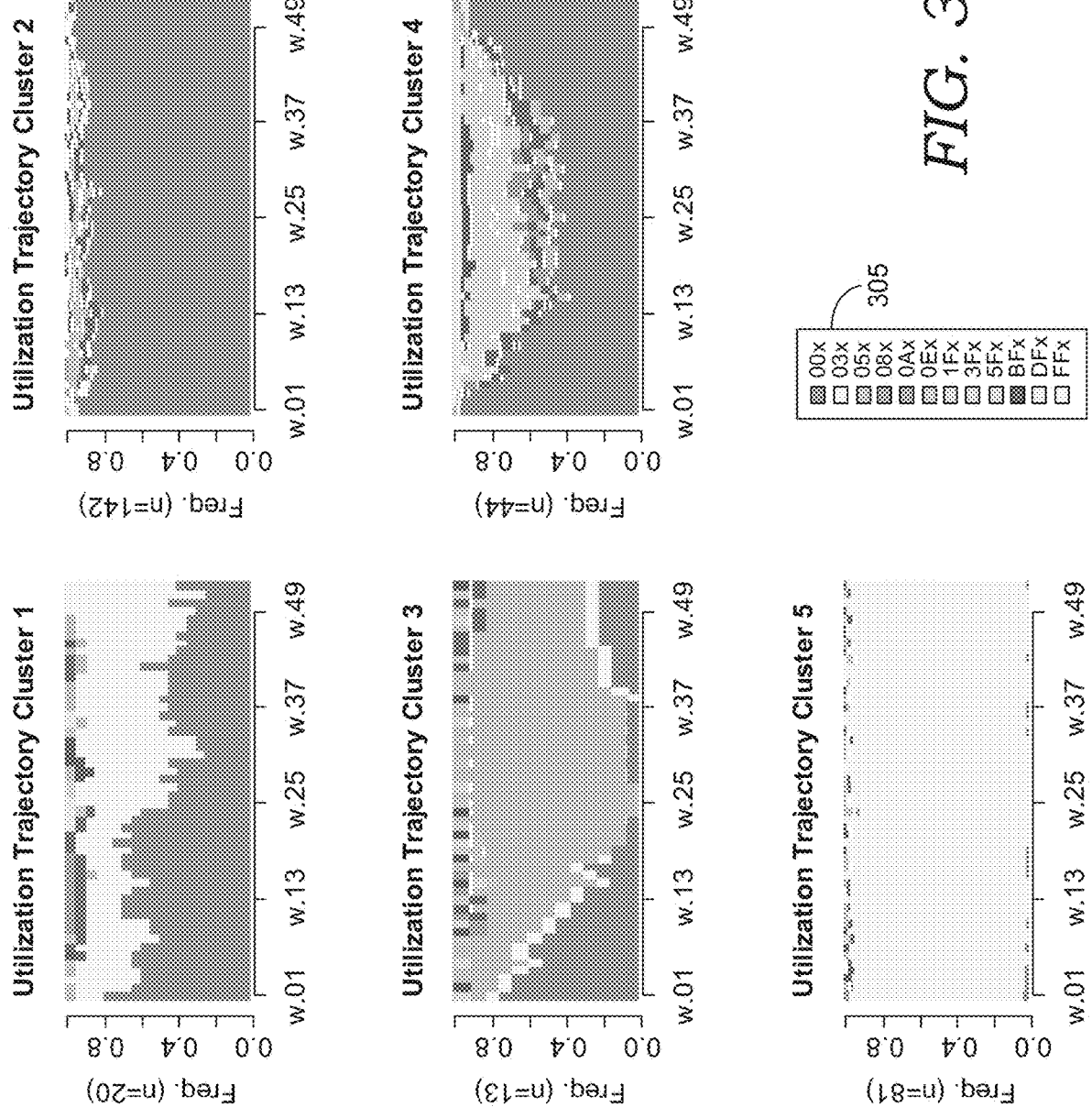
FIG. 3 depicts pattern clusters of example patient condition trajectories.

With reference now to FIGS. 3 and 4, output and results are shown for an example embodiment of the invention as applied to a health care population. In this example records were randomly selected from a patient health records data warehouse, which was derived from Cerner electronic health record (EHR) from 100% of episodes of care that are incident upon participating health care institutions. Personally-identifiable information was removed in conformance with U.S. HIPAA law and regulations, and the de-identified data were stored in a separate, secure database. A 52-week interval of information for a total of 300 representative cases was extracted. The large number of acute conditions and recurrences of exacerbations of chronic conditions make these particularly well-suited to such quantitative analysis.

Each condition is date-stamped according to the time of condition and time of resolution of the condition and recovery. We recast the data in the form of sequences with week-level granularity, and analyzed the sequences using the open-source R statistical trajectory-mining packages TraMineR and arulesSequences of software services 126 of FIG. 1A.

Application of embodiments of the invention in this instance were able to correctly and automatically establish clusters and cluster-membership and cluster-distance values for example candidate records and were also able to automatically detect characteristic differences in conditions that are associated with particular conditions associated with patients having certain attributes, and acute-care episode exposures by patient attribute. Moreover, the system and method embodiments automatically discover statistically significant 'trajectories' (sequences of consecutive conditions) that may be actionable and amenable to training or rehabilitation interventions specially designed to interdict or prevent the significant trajectories or patterns.

Turning to FIG. 3, illustrative examples of pattern clusters, such as generated by step 240 of method 200, based on the patient data, are provided. In particular, FIG. 3 shows 5 example clusters of serial condition trajectories, labeled Utilization Trajectory Cluster 1 ("cluster #1") through Utilization Trajectory Cluster 5 ("cluster #5"). A legend 305 indicates which complexity scores correspond to the colors of clusters 1 through 5 of FIG. 3.

With reference to FIG. 3, Cluster #2 includes a 50% proportion of patients who, despite having 2 or more chronic conditions and despite minimal ambulatory medication intensity or complexity as measured by the Medication Complexity Index (MCI), manage to avoid accessing the acute-care health system for more than 80% of the 52 weeks in the year. Thus, it is unlikely that substantial improvements in utilization rate could be made here. Accordingly, we might consider this a "baseline" repeat-condition pattern.

Cluster #4 consists of 15% of patients in whom pharmacologic management of chronic conditions was infrequent or had poor adherence. It is possible that meaningful changes in prevention or case-management or other factors could yield significant reduction in this group. Cluster #5 represents approximately 25% of patients who had greater case-management and continuity of ambulatory medications and slightly more intensive pharmacologic management of their multiple chronic conditions, resulting in markedly reduced rate of emergency department episodes and in-patient admissions to hospital. Cluster #1 involves 7% of patients with chronic conditions of moderate to high severity as reflected by the acute-care COMPRI score, but the episodes are repeated and of such cumulative duration as to constitute a major annual impact to the providers of health services.

Cluster #3 represents a 5% subgroup of patients whose condition trajectories are diverse with large variability, higher complexity of medication regimen, and approximately 4 times higher acute-care episode rate compared to cluster #2. It is likely that detailed analysis of this group may reveal behavioral differences that would be amenable to education and preventive steps to reduce risk in patients who exhibit this pattern, including efforts to simplify the medications regimen.

In all instances, the matching of a patient's condition-trajectory against the patterns represented by these clusters can reliably guide the prescribing of a specific intervention to mitigate the risks that are associated with the cluster to which the player belongs.

Although the invention has been described with reference to the embodiments illustrated in the attached drawing figures, it is noted that substitutions may be made and equivalents employed herein without departing from the scope of the invention as recited in the claims. For example, additional steps may be added and steps omitted without departing from the scope of the invention.

Many different arrangements of the various components depicted, as well as components not shown, are possible without departing from the spirit and scope of the present invention. Embodiments of the invention have been described with the intent to be illustrative rather than restrictive. Alternative embodiments will become apparent to those skilled in the art that do not depart from its scope. A skilled artisan may develop alternative means of implementing the aforementioned improvements without departing from the scope of the invention.

By way of example, variations of some embodiments may be applied to enhance computerized physician order entry (CPOE) by providing context-awareness and recommending patient-specific orders. In particular, some embodiments of this example may be applied to facilitate more accurate and efficient identification of diagnostic or therapeutic orders for a patient. These particular embodiments, referred to herein as embodiments for order recommendation or order recommender, provide patient order recommendation services by utilizing the complex trajectory mining and trajectory-cluster discovery, such as described above. For example, some embodiments for order-recommendation can match a particular population of patients to a candidate patient having similar conditions or multiple episodes or encounters over a period of time, and then identify frequent itemsets or information comprising orders and the parameters of those orders that are frequent co-associated items.

Taking a closer look at the problems addressable by embodiments of the order recommender, CPOE is complicated by the sheer number of available orders and parameters. An order catalog may have over 10,000 different entries in various departments, and the formulary for medications is several thousand medications long. To reduce complexity on the caregiver-user or caregiver-prescriber, many healthcare institutions have implemented various solutions attempting to help the caregiver-user figure out what to do with the patient. Some solutions limit orders available to the caregiver-user via CPOE-interface to shorter lists of pre-determined items. Some solutions identify orders that are commonly issued by other patients with this condition, for example if the patient is a heart-failure patient, then what do we typically order for heart-failure patients. But such attempts lack any context-awareness of the patient and tend not to promote newer treatments. Other solutions sold as "order sets" are just lists of things that may lack any specificity such as parameters for an order set including the dosing and frequency, if it is a drug, for example. Further, such order sets may be prepared by self-designated experts or top leaders who may have strong opinions about what should be done for particular circumstances. This can stifle innovation because recommendations may become stale over time as newer options are excluded. Such solutions lack diversity in prescribing and the creativity which surrounds that by which new, previously unrecognized safe and effective orders can be identified, as may be provided by some embodiments of the order-recommender.

Embodiments of the order recommender may provide shorter lists for the caregiver-user that can be automatically generated and include order sentences, with dosage, frequency, or other parameters, so that the caregiver-user can more easily look at the list and click on the items that are relevant, rather than scrolling through a longer list or selecting inferior items. Additionally embodiments mitigate a commonly occurring problem where doctors fail to update problem lists sufficiently near interactive ordering time.

Embodiments of the order recommender take advantage of recent order history for a particular patient plus other contextual information such as patient_type, provider_role, venue, payor/plan, and other variables that may be used for clustering. In some cases, embodiments apply a frequent-sequence mining algorithm wherein matching sequences are identified. This can include identifying inter-event patterns such as matching subsequences of clinical events, from sequentially occurring clinical events, which may occur in a contiguous sequence or serially but spaced apart by other clinical events not part of the subsequence. For example, a first patient with a sequence of clinical events A, B, C, D, E and a second patient with sequence of clinical events A, R, P, C, D, S may be determined to have a matching inter-event pattern (or salient sequence) comprising the sequence A, C, D (event A followed by event C and then event D), in some embodiments. Thus, embodiments of the order recommender can return a shorter list of items virtually all of which are likely to be germane to the caregiver-prescriber's current ordering decisions for the present patient, taking all of the context information into account. For example, only items relevant to where the candidate patient currently is in terms of position-within-trajectory are shown to the caregiver. Specifically, if there are severity-based or step/escalation-therapy regimes (either payor-mandated or de facto informal ones), embodiments may determine automatically where the patient is positioned in that sequence or trajectory. In other words, it does not suggest items that would have been relevant to people with the patient's condition or diagnosis at an earlier stage in the treatment of that condition. Some embodiments may thus recommend an individual order that is fully parameterized without any need for the caregiver to determine dosage, for example; he or she only need select the order.

Some embodiments utilize the trajectory miner or TraMineR R-system module or a similar service to identify which cluster a candidate patient belongs, and further when they're in the identified cluster, what is their stage or severity, and within that what are the frequent itemsets associated with that sub-cluster that might be relevant to affect the recommendation for the candidate patient. The trajectory and slope of severity for a patient condition may change over time. Therefore, some embodiments identify time-oriented clusters for which the candidate patient is a member to provide the greater degree of context awareness.

Embodiments of the order recommender may be implemented using an open-source package in R, which can be embedded in two classes of software agents, in a multi-agent computer system such as described above in connection to FIG. 1A. A first class to handle the stream-listener 'discovery'/'sequence-indexing-and-frequent-sequence-winnowing'-time processing; and a second class to handle the 'current-patient-match-against-frequent-sequences' time processing during interactive CPOE.

Figure 8:
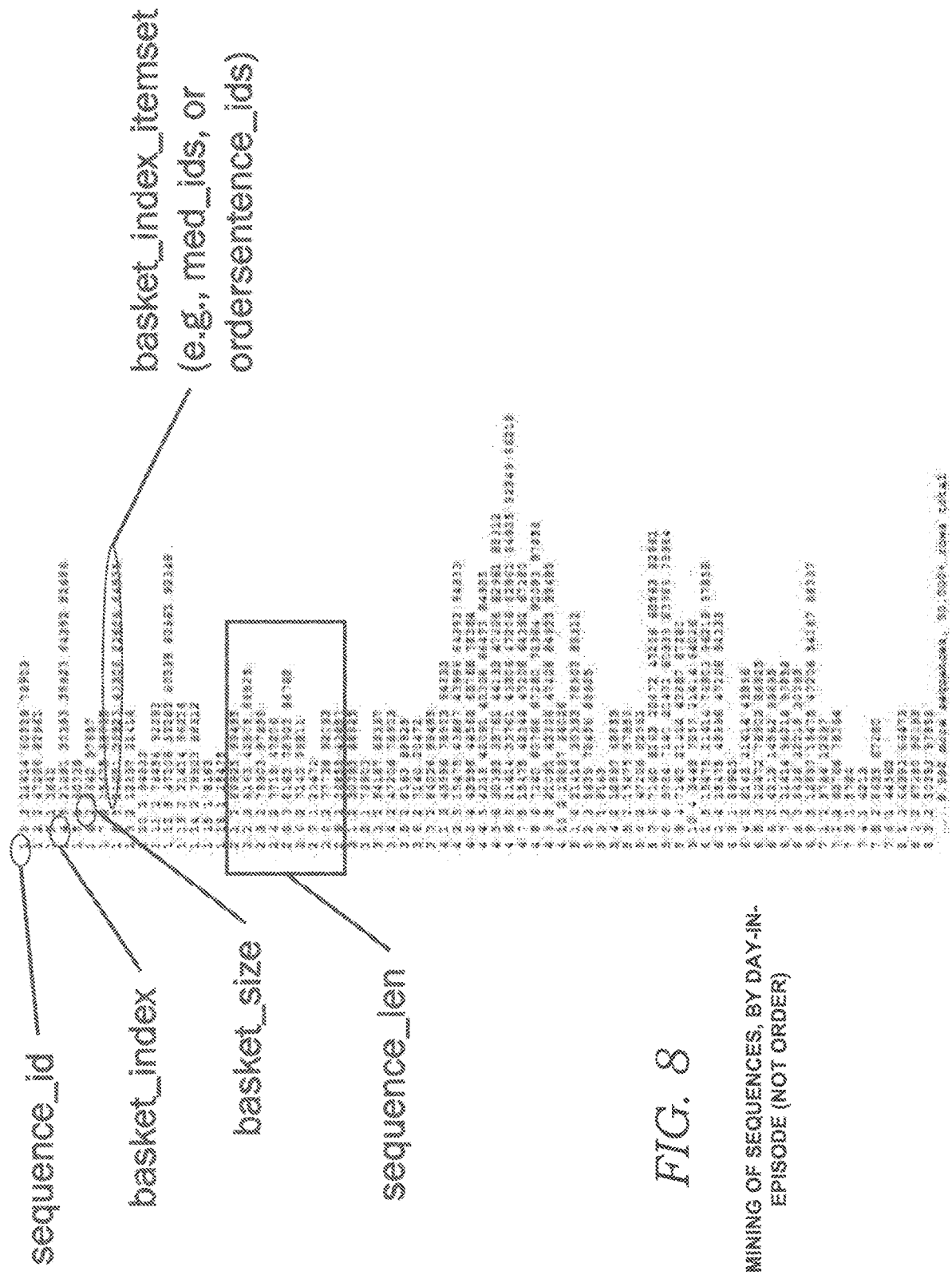
FIG. 8 illustratively shows applying a variation of one embodiment for mining of patient order sequences.

Turning now to FIGS. 8 and 9, with reference to FIG. 8, an illustrative depiction of mining of sequences by day-in-episode (not order) is provided. With reference to FIG. 9, an illustrative example is provided showing matching sequences of a candidate patient to a cluster in order to determine baskets of orderables are later in time. Such information may be useful for planning and budgeting in addition to more effectively treating the patient and reducing complexity on the caregiver-prescriber.

Example reductions-to-practice of embodiments of the order recommender have been applied to in-patient acute-care medication ordering on (a) community-acquired pneumonia (CAP) cases and (b) COPD cases. Specifically, the COPD frequent-sequence itemsets involve inhaled corticosteroids, short-acting beta-agonists, long-acting beta-agonists, tachycardia management, pulmonary hypertension management with (PDE5 inhibitors like Adcirca; endothelin blockers like Tracleer; prostaglandins like Ventavis), and heart failure management. The CAP frequent-sequence itemsets involve beta-lactam, fluoroquinolone, macrolide, ketolide, and other antibiotics, additional meds in non-responders, 'adjunctive' meds (tifacogin; corticosteroids; etc.) in more severe cases, influenza/pneumococcal vaccines, and ARDS-related drugs in patients sick enough to be put on ventilator.

It will be understood that certain features and subcombinations are of utility and may be employed without reference to other features and subcombinations and are contemplated within the scope of the claims. Not all steps listed in the various figures need be carried out in the specific order described.

Accordingly, in one aspect, an embodiment of the invention is directed to a computer-implemented method for identifying temporal trajectory clusters in a longitudinal time series database comprised of a plurality of records arranged in rows and columns. The method includes assigning a unique identifier to all records in the database; retrieving the date-time stamps associated with each condition episode record and condition-recovery duration, creating a blocking subset of between 1 and all of the columns in the database, wherein the variables comprise at least one of payor group, age, cumulative encounters with law enforcement per multi-year time period, whether the patient has dementia, other patient diagnoses having a bearing on cognition or adhearance, and calculating the entropy index values of each conditions time series retrieved. The method further includes calculating a plurality of K-nearest-neighbor clusters of the retrieved condition time series records; and calculating trajectory distances between an individual patient's record and the centroids of each of the clusters. In some embodiments of the method, applying a pair-wise matching algorithm step further comprises matching a candidate record X against the clusters thus identified, by comparisons of distances and entropies against heuristic threshold values, and in some embodiments, the candidate matches are sorted in increasing distance order.

In another aspect, one or more computer-readable media having computer-usable instructions embodied thereon that, when executed, enable a given processor to perform a method for discovering context-specific serial condition trajectories. The method includes receiving target information associated with a target population of patients from a first set of records of a health-records system, receiving reference information associated with a reference population of patients from a second set of records of the health-records system, receiving attribute information specifying one or more attributes of interest, and based on the received target and attribute information, determining a set of timeseries, each timeseries comprising acute-care episode complexity information for an entity of the target population. The method also includes from the timeseries, determining a set of timeseries trajectory clusters, wherein each cluster has associated with it a centroid, for a first health record from the first set of health records, determining a first health record cluster distance separating the first health record from the centroid of a first trajectory cluster of the set of clusters, and determining a distance threshold of cluster distance. The method further includes performing a comparison of distance threshold and first health record cluster distance, and based on the comparison, determining that the first health record is a match to the first trajectory cluster.

In some embodiments of the method, determining a set of time series comprises determining a set of blocking variables present the target and reference information, wherein each blocking variable has a value associated with it, extracting from the target information, a candidate set of health records containing values lexically similar to values of blocking variables, for each member of the candidate set, extracting date-time coordinates for episodes, and computing inter-episode time intervals between the episodes, and assembling the intervals as timeseries associated with each health record of the candidate set. In some embodiments, the method further comprises determining an entropy index for each trajectory cluster in the set of trajectory clusters. In some embodiments, the cluster of the set of trajectory clusters is displayed to a caregiver, and in some embodiments an entropy index is displayed to a caregiver.

Further, in some embodiments, the method further comprises based on a determination that the first health record is a match to the first trajectory cluster, identifying a care regimen for a patient associated with the first health record, and in some embodiments the method further comprises based on a determination that the first health record is a match to the first trajectory cluster, determining a likelihood of risk of future acute-care episode for a patient associated with the first health record. In some embodiments, the method further comprises based on a determination that the first health record is a match to the first trajectory cluster, predicting a level of health care resources likely to be utilized by a patient associated with the first health record, and in some embodiments the method further comprises based on a determination that the first health record is a match to the first trajectory cluster, estimating a future cost for providing health care services to a patient associated with the first health record.

In yet another aspect, a system for discovering context-specific serial condition trajectories is provided. The system comprises one or more processors coupled to a computer storage medium, the computer storage medium having stored thereon a plurality of computer software components executable by the processor, the computer software components. The computer software components comprise a target information component that receives target information associated with a target population of patients from a first set of records of a health-records system, a reference information component that receives reference information associated with a reference population of patients from a second set of records of the health-records system, an attribute information component that receives attribute information specifying one or more attributes of interest, and a timeseries component that determining a set of timeseries based on the received target and attribute information, each timeseries comprising acute-care episode complexity information for an entity of the target population. The computer software components also comprise a trajectory cluster component that determines from the timeseries a set of timeseries trajectory clusters, wherein each cluster has associated with it a centroid, a distance component that determines, for a first health record from the first set of health records, a first health record cluster distance separating the first health record from the centroid of a first trajectory cluster of the set of clusters, and a threshold component that determines a distance threshold of cluster distance. The computer software components further comprise a comparison component that performs a comparison of distance threshold and first health record cluster distance; and a match component that determines that the first health record is a match to the first trajectory cluster based on the comparison.

In some embodiments, the system further comprises an entropy index component that determines an entropy index for each trajectory cluster in the set of trajectory clusters, a display component that displays a cluster, of the set of trajectory clusters, to a caregiver, a display component that displays an entropy index to a caregiver, and/or a regimen component that identifies a care regimen for a patient associated with the first health record based on a determination that the first health record is a match to the first trajectory cluster. In some embodiments, the system further comprises a likelihood component that determines a likelihood of risk of future acute-care episode for a patient associated with the first health record based on a determination that the first health record is a match to the first trajectory cluster, a prediction component that predicts a level of health care resources likely to be utilized by a patient associated with the first health record, based on a determination that the first health record is a match to the first trajectory cluster, and/or a cost estimating component that estimates a future cost for providing health care services to a patient associated with the first health record, based on a determination that the first health record is a match to the first trajectory cluster.

The invention claimed is:

1. A computer-implemented method to determine a recommendation for treating community acquired pneumonia (CAP) in a population of humans with CAP, the method comprising:

for a candidate patient, determining, by a computer processor, a set of health records stored on at least one data store for a population of reference patients having conditions, multiple episodes, or encounters over a period of time similar to the candidate patient, wherein each reference patient health record forms a reference set of clinical event sequences;

receiving, by the computer processor, candidate patient information associated with the candidate patient, the candidate patient information including a patient sequence of clinical events;

creating a candidate patient data frame based on the received candidate patient information;

generating, by the computer processor, at least one timeseries for the candidate patient based on the candidate patient data frame, the at least one timeseries including one or more complexity indicators;

based on the at least one timeseries for the candidate patient, determining, by the computer processor, a candidate patient condition trajectory;

determining, by the computer processor, an inter-event pattern present in the set of health records of the reference patients by performing a comparison of the candidate patient condition trajectory and the reference set of clinical event sequences to determine a matching set of clinical event sequences, the inter-event pattern determination is accomplished in part by determining a set of timeseries trajectory clusters by performing a database scan of the at least one data store, applying a multi-cluster model, and extracting one or more cluster assignments, wherein each timeseries trajectory cluster has a centroid;

based in part on the inter-event pattern for the reference patients, automatically determining, by the computer processor, the recommendation for treatment for CAP based in part on a matching of clinical event sequences; and presenting an indication for the recommendation via a clinician interface.

2. The method of claim 1 wherein determining the inter-event pattern includes calculating timeseries trajectory clusters and entropy indexes.

3. The method of claim 1 wherein the inter-event pattern includes clinical events for orders or beta-lactam, fluoroquinolone, macrolide, or ketolide.

4. The method of claim 1 wherein the recommendation comprises one or more orders including order sentence, dosage, or frequency information.

5. The method of claim 1 determining one or more frequently occurring baskets of order-events present in the matching set of clinical event sequences; and
- based on the one or more frequently occurring baskets, determining a set of order recommendations for the candidate patient.

6. The method of claim 1 wherein the matching set of clinical event sequences is ranked by cluster distance.

7. The method of claim 6 wherein the recommendation comprises one or more orders including order sentence, dosage, or frequency information.

8. The method of claim 1 wherein the reference set of clinical event sequences comprises conditions, multiple episodes, or encounters over a period of time.

9. The method of claim 1 wherein the matching comprises comparing inter-event patterns in the at least one timeseries for the candidate patient to inter-event patterns in the reference set of clinical event sequences.

10. The method of claim 1 further comprising providing the recommendation for the candidate patient to a caregiver.

11. The method of claim 2 wherein the matching comprises comparing subsequences in the at least one timeseries for the candidate patient to subsequences in the reference set of clinical event sequences.

12. The method of claim 1 wherein the reference set of clinical event sequences that is similar to the patient sequence of clinical events comprises a subset of the reference set of clinical event sequences having one or more salient sequences in common with the patient sequence of clinical events.

13. One or more non-transitory computer-readable media having computer-usable instructions embodied thereon that, when executed, enable a given processor to perform a method for facilitating clinical decision-making, the method comprising:
- for a candidate patient, determining, by a computer processor, a set of health records stored on at least one data store for a population of reference patients having conditions, multiple episodes, or encounters over a period of time similar to the candidate patient, wherein each reference patient health record forms a reference set of clinical event sequences;
- receiving, by the computer processor, candidate patient information associated with the candidate patient, the candidate patient information including a patient sequence of clinical events;
- creating a candidate patient data frame based on the received candidate patient information;
- generating, by the computer processor, at least one timeseries for the candidate patient based on the candidate patient data frame, the at least one timeseries including one or more complexity indicators;
- based on the at least one timeseries for the candidate patient, determining, by the computer processor, a candidate patient condition trajectory;
- determining, by the computer processor, an inter-event pattern present in the set of health records of the reference patients by performing a comparison of the candidate patient condition trajectory and the reference set of clinical event sequences to determine a matching set of clinical event sequences, the inter-event pattern determination is accomplished in part by determining a set of timeseries trajectory clusters by performing a database scan of the at least one data store, applying a multi-cluster model, and extracting one or more cluster assignments, wherein each timeseries trajectory cluster has a centroid;
- based in part on the inter-event pattern for the reference patients, automatically determining, by the computer processor, a recommendation for treatment for community acquired pneumonia (CAP) based in part on a matching of clinical event sequences; and
- presenting an indication for the recommendation via a clinician interface.

14. The computer-readable media of claim 13 further comprising:
- identifying health records for the candidate patient, the health records including a sequence of clinical events that matches a reference cluster.

15. The computer-readable media of claim 14 further comprising:
- designating the candidate patient as a candidate for having CAP.

16. The computer-readable media of claim 13, wherein the reference set of clinical event sequences comprises conditions, multiple episodes, or encounters over a period of time.

17. The computer-readable media of claim 16, wherein an encounter comprises one or more treatments, diagnoses, orders, or caregiver actions.

18. A computer-implemented system to determine a recommendation for treating community acquired pneumonia (CAP) in a population of humans with CAP, the system comprising:
- one or more data processors; and
- one or more non-transitory computer-readable storage media containing instructions which when executed on the one or more data processors, cause the one or more data processors to perform operations including:
- for a candidate patient, determining a set of health records stored on at least one data store for a population of reference patients having conditions, multiple episodes, or encounters over a period of time similar to the candidate patient, wherein each reference patient health record forms a reference set of clinical event sequences;
- receiving candidate patient information associated with the candidate patient, the candidate patient information including a patient sequence of clinical events;
- creating a candidate patient data frame based on the received candidate patient information;
- generating at least one timeseries for the candidate patient based on the candidate patient data frame, the at least one timeseries including one or more complexity indicators;
- based on the at least one timeseries for the candidate patient, determining a candidate patient condition trajectory;
- determining an inter-event pattern present in the set of health records of the reference patients by performing a comparison of the candidate patient condition trajectory and the reference set of clinical event sequences to determine a matching set of clinical event sequences, the inter-event pattern determination is accomplished in part by determining a set of timeseries trajectory clusters by performing a database scan of the at least one data store, applying a multi-cluster model, and extracting one or more cluster assignments, wherein each timeseries trajectory cluster has a centroid;
- based in part on the inter-event pattern for the reference patients, automatically determining, by the one or more data processors, the recommendation for treatment for CAP based in part on a matching of clinical event sequences; and presenting an indication for the recommendation via a clinician interface.

19. The computer-implemented system of claim 18, wherein the health records of the population of reference patients comprises conditions, multiple episodes, or encounters over a period of time.

20. The computer-implemented system of claim 18, wherein a candidate complexity record is assembled into a timeseries format.

* * * * *